US010690498B2

(12) United States Patent
Turner et al.

(10) Patent No.: US 10,690,498 B2
(45) Date of Patent: Jun. 23, 2020

(54) AUTOMATIC POINT LAYOUT AND STAKING SYSTEM

(71) Applicant: Trimble, Inc., Sunnyvale, CA (US)

(72) Inventors: Jamin Michael Turner, Arcanum, OH (US); Kevin Marc Morrissey, Xenia, OH (US); Chris William Snyder, Union City, OH (US); Ayman Zuhdi Hajmousa, Dayton, OH (US)

(73) Assignee: Trimble, Inc., Sunnyvale, CA (US)

( * ) Notice: Subject to any disclaimer, the term of this patent is extended or adjusted under 35 U.S.C. 154(b) by 436 days.

(21) Appl. No.: 15/591,213

(22) Filed: May 10, 2017

(65) Prior Publication Data
US 2018/0328729 A1 Nov. 15, 2018

(51) Int. Cl.
*G01C 15/00* (2006.01)
*G01S 19/13* (2010.01)
*G01B 11/00* (2006.01)
*G01S 17/89* (2020.01)
*G01S 7/481* (2006.01)
*G01C 15/02* (2006.01)
(Continued)

(52) U.S. Cl.
CPC .......... *G01C 15/004* (2013.01); *G01B 11/002* (2013.01); *G01C 15/002* (2013.01); *G01C 15/02* (2013.01); *G01S 1/70* (2013.01); *G01S 7/4813* (2013.01); *G01S 17/89* (2013.01); *G01S 19/13* (2013.01); *A61B 6/08* (2013.01); *A61B 6/587* (2013.01)

(58) Field of Classification Search
CPC .... G01C 15/004; G01C 15/002; G01C 15/02; G01S 7/4813; G01S 17/89; G01S 19/13; G01B 11/002; A61B 6/08; A61B 6/587
See application file for complete search history.

(56) References Cited

U.S. PATENT DOCUMENTS

| 4,029,415 A | 6/1977 | Johnson |
| 4,035,084 A | 7/1977 | Ramsay |

(Continued)

FOREIGN PATENT DOCUMENTS

| DE | 69122965 T2 | 3/1992 |
| DE | 69224671 T2 | 3/1994 |

(Continued)

*Primary Examiner* — Nimeshkumar D Patel
*Assistant Examiner* — Tania Courson
(74) *Attorney, Agent, or Firm* — Frederick H. Gribbell; Russell F. Gribbell; Aaron S. Brodsky

(57) ABSTRACT

An automatic point layout system identifies points and their coordinates using vertical planes of laser light. Laser controllers aim vertical laser light planes that will cross at any desired point on the jobsite floor. The user views a virtual jobsite illustration on a remote controller touchscreen display, and selects a point of interest. Commands are sent to the two laser controllers, which aim their laser transmitters at that point of interest, showing visible laser light lines that intersect directly at the point of interest, for staking. The user selects a second point of interest on the touchscreen display, commanding the laser transmitters to rotate to a new set of coordinates. The user performs these functions seamlessly; the remote controller allows the user to quickly move from one point of interest to the next, without having changing to any other operating mode between the identifying and staking of each new point.

24 Claims, 28 Drawing Sheets

(51) Int. Cl.
  *G01S 1/70* (2006.01)
  *A61B 6/00* (2006.01)
  *A61B 6/08* (2006.01)

(56) References Cited

U.S. PATENT DOCUMENTS

| | | | |
|---|---|---|---|
| 4,598,481 A | 7/1986 | Donahue | |
| 4,820,041 A | 4/1989 | Davidson | |
| 4,836,671 A | 6/1989 | Bautista | |
| 5,076,690 A | 12/1991 | deVos | |
| 5,100,202 A | 3/1992 | Hughes | |
| 5,100,229 A | 3/1992 | Lundberg | |
| 5,110,202 A | 5/1992 | Dornbusch | |
| 5,137,354 A | 8/1992 | deVos | |
| 5,229,828 A * | 7/1993 | Wiklund | G01C 15/00 356/141.1 |
| 5,243,398 A | 9/1993 | Nielsen | |
| 5,272,814 A | 12/1993 | Key | |
| 5,294,970 A | 3/1994 | Dornbusch | |
| 5,313,409 A * | 5/1994 | Wiklund | G01C 15/002 33/290 |
| 5,539,990 A | 7/1996 | Le | |
| 5,579,102 A | 11/1996 | Pratt | |
| 5,588,216 A | 12/1996 | Rank et al. | |
| 5,598,269 A | 1/1997 | Kitaevich | |
| 5,671,160 A * | 9/1997 | Julian | G01C 15/00 33/293 |
| 5,828,057 A * | 10/1998 | Hertzman | G01S 7/499 250/225 |
| 5,864,956 A | 2/1999 | Dong | |
| 5,983,510 A | 11/1999 | Wu et al. | |
| 6,034,722 A * | 3/2000 | Viney | G01C 1/04 348/135 |
| 6,035,254 A * | 3/2000 | Nichols | G01C 1/02 701/300 |
| 6,035,540 A | 3/2000 | Wu et al. | |
| 6,115,112 A * | 9/2000 | Hertzman | G01S 7/487 356/5.01 |
| 6,140,957 A | 10/2000 | Wilson | |
| 6,175,328 B1 * | 1/2001 | Ericsson | G01C 15/00 342/357.31 |
| 6,182,372 B1 * | 2/2001 | Lamm | G01C 1/02 33/290 |
| 6,263,004 B1 * | 7/2001 | Arvidsson | H01S 3/0627 372/11 |
| 6,369,755 B1 * | 4/2002 | Nichols | G01C 15/002 342/357.52 |
| 6,381,006 B1 * | 4/2002 | Ramstrom | G01C 15/002 356/141.1 |
| 6,421,627 B1 * | 7/2002 | Ericsson | E02F 3/842 356/139.05 |
| 6,501,543 B2 | 12/2002 | Hedges | |
| 6,545,749 B1 * | 4/2003 | Andersson | G01C 3/08 356/4.01 |
| 6,545,751 B2 | 4/2003 | Beliveau | |
| 6,763,595 B1 | 7/2004 | Hersey | |
| 7,110,092 B2 | 9/2006 | Kasper | |
| 7,145,648 B2 * | 12/2006 | Vogel | G01C 1/04 356/141.4 |
| 7,148,958 B2 | 12/2006 | Ohtomo | |
| 7,168,174 B2 * | 1/2007 | Piekutowski | E01C 19/006 33/1 CC |
| 7,199,872 B2 * | 4/2007 | Van Cranenbroeck | G01C 15/002 356/139.01 |
| 7,552,539 B2 * | 6/2009 | Piekutowski | E01C 19/006 33/1 CC |
| 7,583,373 B2 * | 9/2009 | Schwarz | G01C 15/00 356/141.2 |
| 7,644,505 B2 | 1/2010 | Zeng | |
| 7,646,339 B2 * | 1/2010 | Green | G01C 15/00 342/357.27 |
| 7,679,727 B2 | 3/2010 | Benz et al. | |
| 7,992,310 B2 | 8/2011 | Litvin | |
| 8,087,176 B1 | 1/2012 | Hayes | |
| 8,229,166 B2 * | 7/2012 | Teng | G06T 7/20 382/103 |
| 8,269,984 B2 | 9/2012 | Hinderling | |
| 8,281,495 B2 | 10/2012 | Hayes | |
| 8,307,562 B2 | 11/2012 | Bascom | |
| 8,319,950 B2 * | 11/2012 | Snyder | G01S 7/51 356/3.01 |
| 8,482,721 B2 * | 7/2013 | Snyder | G01S 7/51 356/3.01 |
| 8,553,212 B2 | 10/2013 | Jaeger | |
| 8,595,946 B2 | 12/2013 | Hayes | |
| 8,605,274 B2 * | 12/2013 | Schumacher | G01C 15/004 356/140 |
| 8,943,701 B2 * | 2/2015 | Hayes | G01C 15/002 33/280 |
| 9,182,229 B2 * | 11/2015 | Grasser | G01C 15/00 |
| 9,316,496 B2 * | 4/2016 | Green | G01C 15/002 |
| 9,341,473 B2 * | 5/2016 | Zogg | G01C 15/002 |
| 9,377,298 B2 * | 6/2016 | Zogg | G01C 15/002 |
| 9,377,303 B2 * | 6/2016 | Giger | G01C 15/002 |
| 9,428,885 B2 * | 8/2016 | Nau | E02F 9/261 |
| 9,470,511 B2 * | 10/2016 | Maynard | G01B 11/14 |
| 9,880,022 B1 * | 1/2018 | Unger | G01C 15/002 |
| 9,903,715 B2 * | 2/2018 | Kotzur | G01C 1/04 |
| 9,939,263 B2 * | 4/2018 | Green | G01C 3/08 |
| 9,970,762 B2 * | 5/2018 | Moller | G01C 15/002 |
| 10,007,270 B2 * | 6/2018 | Mazur | E02F 9/2054 |
| 10,113,871 B2 * | 10/2018 | Ang | G01C 15/06 |
| 10,119,818 B2 * | 11/2018 | Maar | G01C 15/06 |
| 10,145,676 B2 * | 12/2018 | Hayes | G01C 15/002 |
| 10,190,288 B2 * | 1/2019 | Matson | G01C 9/06 |
| 10,310,054 B2 * | 6/2019 | Troy | G01S 5/16 |
| 10,337,865 B2 * | 7/2019 | Green | G01C 15/002 |
| 2004/0177523 A1 | 9/2004 | Chang et al. | |
| 2005/0102063 A1 | 5/2005 | Bierre | |
| 2006/0179672 A1 | 8/2006 | Tacklind | |
| 2006/0280212 A1 | 12/2006 | Lu et al. | |
| 2012/0186088 A1 | 7/2012 | Amor | |
| 2012/0198711 A1 | 8/2012 | Hayes | |
| 2012/0236320 A1 * | 9/2012 | Steffey | G01B 11/002 356/614 |
| 2015/0037045 A1 * | 2/2015 | Dumoulin | G01C 15/004 398/162 |
| 2015/0039269 A1 * | 2/2015 | Mejegard | G06Q 10/06 702/182 |
| 2018/0122091 A1 * | 5/2018 | Herbst | G01C 15/002 |
| 2018/0124330 A1 * | 5/2018 | Herbst | G01C 11/00 |
| 2018/0202805 A1 * | 7/2018 | Unger | G01C 15/006 |
| 2019/0056215 A1 * | 2/2019 | Hayes | G01C 15/002 |

FOREIGN PATENT DOCUMENTS

| | | |
|---|---|---|
| DE | 19527829 A1 | 1/1997 |
| DE | 19648626 A1 | 5/1998 |
| DE | 102011077080 | 12/2011 |
| EP | 2226610 A1 | 9/2010 |
| JP | 10239057 | 9/1998 |
| WO | WO 2009053085 | 4/2009 |

* cited by examiner

AUTOMATIC POINT LAYOUT AND STAKING SYSTEM

CROSS-REFERENCE TO RELATED APPLICATIONS

None.

TECHNICAL FIELD

The technology disclosed herein relates generally to layout "surveying" equipment and is particularly directed to an automatic point layout and staking system of the type which identifies points and their coordinates, and transfers identified points on a physical jobsite surface using intersecting vertical planes of laser light. Embodiments are specifically disclosed using at least two laser controllers each having a laser light transmitter and certain laser light sensors, and with a remote controller that acts as a user interface with a touchscreen display, to control certain functions.

When the system is set up, it is capable of aiming each of the vertical laser light planes that are output from the laser transmitters so that projected lines of laser light will cross on the surface at any desired point on the jobsite floor. The user can view a virtual jobsite illustration as a CAD model file on the remote controller, and can manipulate the display to show any particular portion of the virtual jobsite illustration to select the points of interest.

Once a given point of interest has been selected on the touchscreen display of the remote controller, commands are automatically sent wirelessly to the two laser controllers, and their laser transmitters are automatically aimed at the selected physical point of interest, thereby showing a visible pair of laser light lines that intersect directly at the point of interest. The user can then walk to that site of the intersecting laser light lines and stake that point of interest.

The user can then easily select a second point of interest on the touchscreen display of the remote controller, thereby commanding the laser transmitters to automatically rotate to a new set of coordinates on the virtual jobsite illustration. The laser transmitters will then aim their laser light lines directly at that second point of interest and the user can quickly walk to that point and stake it on the physical jobsite floor. The user can perform these functions seamlessly without having to jump back and forth through different CREATE or LAYOUT modes, since the operating software of the present technology for the remote controller allows the user to quickly move from one point of interest to the next, and to the next, without having to go back to any other operating mode between the identifying and staking of each new point.

STATEMENT REGARDING FEDERALLY SPONSORED RESEARCH OR DEVELOPMENT

None.

BACKGROUND

In today's technology, the process for constructing a building typically begins with an architect designing a virtual building in a CAD model, which is a virtual jobsite illustration created on a computer. The CAD model is a Computer Aided Drafting file, and can be either a two-dimensional or a three-dimensional virtual jobsite illustration.

The need for construction contractors to tie a CAD model to the physical world has been around for as long as CAD models have existed. In the past, the conventional solutions have involved pre-creating points of interest on the CAD model, and then later translating those points to the physical world. Unfortunately, this approach adds extraneous data and at least one extra step to the process. Contractors must first create the points on relevant geometry and then use the point data for their physical world work.

The first step of creating points on relevant geometry involves a procedure in which the contractor must figure out which points of the architect CAD model belong with a particular physical structure to be constructed on the jobsite. For example, in a "global mode" the user must select an area of the jobsite floor and select the appropriate points in a "create" mode (or function). All of the points in that area will be displayed, and the user must mentally use selectivity to determine and select the correct points for the particular structure that the user wishes to be laid out at that time.

In the conventional systems, many users start with a "point list," which is a computer file that includes jobsite coordinates of the points of interest that are to be laid out on the jobsite floor. Often, the point list will be a tabulation of such points of interest in the form of a spreadsheet, with the columns of the spreadsheet containing the point designations, the X-coordinates, and the Y-coordinates (in terms of jobsite coordinates, for example). Another format is for the point list data to be exported to a "CSV file" (a comma separated values file), which can be uploaded to a tablet computer.

The point list could be displayed in a graphical format. However, in the conventional systems, such a graphical file merely displays the relative position of the various points of interest to be laid out, without showing any of the floor plan structure.

Therefore, the user who is performing the actual layout work must attempt to correlate any specific point, or set of points, with a particular structure to be worked on "today." In other words, if the user desires to lay out a specific diagonal wall, then that user must attempt to select the exact points of the graphical "point list" file that correspond to that diagonal wall, without being able to see the floor plan and the points of interest on the same display. This typically requires the user to go back and forth between the point list screen and the architect's virtual jobsite illustration screen, to figure out which precise points belong with a specific structural feature. Most jobsites contain hundreds, if not thousands, of points of interest, so this "back and forth" work is not an easy, or intuitive, task.

After that has occurred, the user will want to actually lay out a particular point of interest, using a "layout mode" (or function). The user would typically zoom in on the tablet computer's display being used to show the CAD model; otherwise the user would not necessarily be able to see the exact point of interest that is being selected, particularly if the geometry of the structure being laid out has any curved surfaces, which would typically cause a large number of points to be displayed that are relatively close to one another on the screen. Zooming in often will be quite necessary to select the correct point.

Unfortunately, once the layout function has occurred, the user must go back to the global mode and zoom back out to see the next portion of the virtual jobsite illustration that will then be selected as a group of points of interest. The correct point must then be selected and then the layout mode (or function) must then be selected so that the user can zoom in and go to the exact correct point that is to be laid out and staked on the jobsite floor.

When using the conventional systems that have been available, the user must go back and forth between a "point create mode" and the "layout mode," for staking each point of interest. There are several different types of architect and layout stations that can perform these types of conventional functions. For example, there is a device known as the "total station" that includes a laser distance meter and has an automated angle measuring sensor to detect the azimuth that the laser distance meter is being pointed at.

In one of the more basic forms of a total station, two persons are required to perform the layout procedure: the first person operates the total station itself, and a second person walks around on the jobsite floor with a prism pole. The prism pole has a retroreflective mirror that the laser distance meter of the total station aims at, and if it sees the prism pole's reflective mirror, then the total station will receive a portion of the laser light back and determine the distance. Since the total station knows where the point of interest is supposed to be (once the total station has been set up on this jobsite floor), it will automatically aim at the correct azimuth angle and wait for the second person to position the prism pole at the correct azimuth and distance. The second user at the total station can read out the distance and let the first user who's moving the prism pole know when the prism pole has been placed correctly. This is a painstaking task, and always requires two human beings for the layout and staking procedure.

A more advanced device is known as a total tracking station (TTS), which also includes a laser distance meter; in the total tracking station only a single user is needed for the layout procedure. This user walks around the jobsite floor with a prism pole and also has a remote computer with a display, which is in communication with the total tracking station. The total tracking station gives directions to the user walking around with the remote computer and the prism pole to guide that person to the correct azimuth and distance for accurately positioning the prism pole. Once that has been accomplished, the user will have the prism pole positioned at the correct point that is to be staked on the jobsite floor. While the total tracking station is definitely an improvement over a "raw" total station, the single user still has no visual aid to let that user know exactly where the prism pole is to be positioned except for the display on the remote computer. And even at that, the procedure for positioning the prism pole is onerous, in and of itself, although construction workers are used to working with those devices, regardless of how time consuming and painstaking it is to work with them.

Yet another type of total station is now available which has a pointing laser. In this type of system, the user does not need to use a prism pole, but instead the total station will literally aim a laser beam at the correct point of interest on the jobsite floor. This is a real advancement as compared to devices that require a prism pole; however, there still are some shortcomings. The main shortcoming is that, for a point of interest that is some distance from the location of the total station with pointing laser, the circular laser beam will hit the jobsite floor and show a relatively lengthy ellipse. For example, the ellipse could be a laser beam that is about 3 inches long. While it might seem a simple task to find the exact center of that ellipse, in practice, when the jobsite accuracy is to be within an eighth of an inch, being able to see that exact center of the ellipse can be rather difficult. So this advanced total station with pointing laser still leaves something to be desired, especially for points of interest that are many feet away from the location of the total station itself.

Regardless of what type of total station is being used, with the conventional software that uses CAD models, the user must still bounce between the "point create mode" and the "layout mode" for each point of interest. That may not seem to be an onerous task, but the user must still zoom in and zoom out for each point that is going to be staked on the jobsite floor. If nothing else, this procedure is time consuming To provide a more detailed description of the conventional sequence of operation that uses a total tracking station will now be presented below, as OUTLINE #1.

OUTLINE #1—SEQUENCE OF OPERATION, using a tracking total station (for example, a Spectra Focus 8 reflectorless total station, Model No. HNA33500), with "Field Link" software, sold by Trimble, Inc. of Sunnyvale, Calif.

(1) Begin setup mode, using CREATE FROM MODEL button, on remote controller.
(2) User views the CAD model two-dimensional display on the remote's screen.
  (2a) This is a virtual jobsite illustration.
(3) User selects the POINT CREATE mode.
  (3a) User "taps" the screen at a point of interest of the CAD model. Options:
    (3a-1) Intersection of lines
    (3a-2) End point of a line
    (3a-3) Mid point of a line
    (3a-4) Center of a circle or an arc
  (3b) User designates a point with a number, such as "#100" for the first control point.
  (3c) User designates a point with a number, such as "#101" for the second control point.
(4) User selects the SETUP mode.
  (4a) Remote controller displays the CAD model (virtual jobsite illustration).
  (4b) User "taps" the screen at the first control point (CP1).
  (4c) User places the prism pole at CP1.
  (4d) User "taps" the "measure" function on the screen.
  (4e) User "taps" the screen at the second control point (CP2).
  (4f) User places the prism pole at CP2.
  (4g) User "taps" the "measure" function on the screen.
  (4h) User "taps" the "SET" function on the screen.
  (4i) The Setup mode is completed.
(NOTE: The system software is ready to start selecting points to be laid out on the jobsite floor.)
(5) For the first point of interest ("n"): the CREATE FROM MODEL mode is selected.
  (5a) User selects the first point, and "taps" the screen (at an intersection, for example).
  (5b) The CAD model software creates a "point icon" at this placement, on the screen.
  (5c) User "taps" the "CREATE" function on the screen.
    (5c-1) The software gives that point a designation, such as "#102".
  (5d) User "taps" the "MEASURE" function on the screen.
(6) The LAYOUT mode is now selected.
  (6a) User "taps" the specific point to be laid out.
  (6b) The tracking total station keeps track of the prism pole as it is being moved.
    (6b-1) The instantaneous location of the prism pole is display on the screen of the remote controller. The user can see this.

(6b-2) The remote controller also displays an instruction bar on the screen.
(6b-3) The instruction bar gives directions to the user where to move the prism pole.
(6b-4) As the prism pole approaches point #102, a hockey puck symbol is displayed.
(6b-5) Once the display shows a green circle, the prism pole is "on point."
(6c) User "taps" the "MEASURE" function on the screen.
(6c-1) This informs the software that the user is staking this point #102.
(7) For the second point of interest ("n+1"): the CREATE FROM MODEL mode is selected.
(7a) User selects the second point, and "taps" the screen (at an end point, for example).
(7b) The CAD model software creates a "point icon" at this placement, on the screen.
(7c) User "taps" the "CREATE" function on the screen.
(7c-1) The software gives that point a designation, such as "#103".
(7d) User "taps" the "MEASURE" function on the screen.
(8) The LAYOUT mode is now selected.
(8a) User "taps" the specific point to be laid out.
(8b) The tracking total station keeps track of the prism pole as it is being moved.
(8b-1) The instantaneous location of the prism pole is display on the screen of the remote controller. The user can see this.
(8b-2) The remote controller also displays an instruction bar on the screen.
(8b-3) The instruction bar gives directions to the user where to move the prism pole.
(8b-4) As the prism pole approaches point #103, a hockey puck symbol is displayed.
(8b-5) Once the display shows a green circle, the prism pole is "on point."
(8c) User "taps" the "MEASURE" function on the screen.
(8c-1) This informs the software that the user is staking this point #103.
(9) For the "next" point of interest ("n+m"): the CREATE FROM MODEL mode is selected.
(9a) User selects the next point, and "taps" the screen (at a mid-point, for example).
(9b) The CAD model software creates a "point icon" at this placement, on the screen.
(9c) User "taps" the "CREATE" function on the screen.
(9c-1) The software gives that point a designation, such as "#103+m".
(9d) User "taps" the "MEASURE" function on the screen.
(10) The LAYOUT mode is now selected.
(10a) User "taps" the specific point to be laid out.
(10b) The tracking total station keeps track of the prism pole as it is being moved.
(10b-1) The instantaneous location of the prism pole is display on the screen of the remote controller. The user can see this.
(10b-2) The remote controller also displays an instruction bar on the screen.
(10b-3) The instruction bar gives directions to the user where to move the prism pole.
(10b-4) As the prism pole approaches point #103+m, a hockey puck symbol is displayed.
(10b-5) Once the display shows a green circle, the prism pole is "on point."
(10c) User "taps" the "MEASURE" function on the screen.
(10c-1) This informs the software that the user is staking this point #103+m.

As can be seen from the above OUTLINE #1, the system for laying out points once the setup has been completed requires the user to bounce between the "CREATE FROM MODEL" mode and the "LAYOUT" mode, for each point of interest to be laid out and then staked.

SUMMARY

Accordingly, it is an advantage to provide a remote controller that can display a virtual jobsite illustration as a CAD model, in which the remote controller has operating software that allows a user to both create and stake points of interest in a single sequence of operations, and then move on to a next point of interest without having to change modes of operation.

It is another advantage to provide a remote controller in a layout and point staking system that allows a user to zoom in on a small portion of a jobsite floor to both create and then lay out a particular point of interest, and then move on to a next point of interest while remaining in the zoomed-in mode on the touchscreen display of the remote controller.

It is yet another advantage to provide an automatic point layout and staking system that provides at least two laser controllers that can each produce a vertical fan beam of laser light to direct a user's attention to specific points on a jobsite floor, while also providing a remote controller with operating software that allows a user to quickly select points of interest on a virtual jobsite illustration (as a CAD model), and then seamlessly move to staking out each point of interest immediately after being selected as a point of interest, and then moving on to the next point of interest without having to change the display mode.

Additional advantages and other novel features will be set forth in part in the description that follows and in part will become apparent to those skilled in the art upon examination of the following or may be learned with the practice of the technology disclosed herein.

To achieve the foregoing and other advantages, and in accordance with one aspect, a method for using a layout and point transfer system is provided, in which the method comprises the following steps: (a) providing at least one laser controller, the at least one laser controller including: (i) a laser light transmitter that emits visible laser light, the laser light transmitter being rotatable about a substantially vertical axis; (ii) an electronic angle measuring instrument; and (iii) a first processing circuit, a first memory circuit, a first wireless communications circuit, and a first input/output interface circuit; (b) providing a remote controller, which includes: a second processing circuit, a second memory circuit, a second wireless communications circuit, a display, a user-controlled input circuit, and a second input/output interface circuit, wherein the at least one laser controller and the remote controller communicate with one another by use of the first and second wireless communications circuits; (c) placing the at least one laser controller on a jobsite surface in a work area, and setting up the at least one laser controller so that, in terms of jobsite coordinates, a position of the at least one laser controller on the jobsite surface is determined; (d) executing a computer program using the remote controller, which displays a virtual jobsite illustration on the display; (e) selecting, using the display and the user-controlled input circuit, a specific point of interest on the virtual jobsite illustration, and virtually staking the specific point of interest on the virtual jobsite illustration; and (f) automatically indicating, on the jobsite surface, the specific point of interest to be staked, by aiming the laser light transmitter of the at least one laser controller directly at an azimuth angle of the specific point of interest on the jobsite surface.

In accordance with another aspect, a method for using a layout and point transfer system is provided, in which the method comprises the following steps: (a) providing a laser controller, the laser controller including: (i) an electronic distance measuring instrument; (ii) an electronic angle measuring instrument; and (iii) a first processing circuit, a first memory circuit, a first wireless communications circuit, and a first input/output interface circuit; (b) providing a remote controller, which includes: a second processing circuit, a second memory circuit, a second wireless communications circuit, a display, a user-controlled input circuit, and a second input/output interface circuit, wherein the laser controller and the remote controller communicate with one another by use of the first and second wireless communications circuits; (c) providing a movable target that is controlled by a human user; (d) placing the laser controller on a jobsite surface in a work area, and setting up the laser controller so that, in terms of jobsite coordinates, a position of the laser controller on the jobsite surface is determined; (e) executing a computer program using the remote controller, which displays a virtual jobsite illustration on the display; (f) selecting, using the display and the user-controlled input circuit, a specific point of interest on the virtual jobsite illustration, and virtually staking the specific point of interest on the virtual jobsite illustration; and (g) automatically indicating the specific physical point of interest to be staked: (i) by aiming the electronic distance measuring instrument of the laser controller directly at the movable target as the human user moves the movable target; (ii) by providing directions to the user to guide movements of the movable target toward the specific point of interest on the jobsite surface; and (iii) by providing an indication to the user that the movable target is now placed at the specific point of interest on the jobsite surface.

In accordance with yet another aspect, a method for using a layout and point transfer system is provided, in which the method comprises the following steps: (a) providing a laser controller, the laser controller including: (i) an electronic distance measuring instrument; (ii) an electronic angle measuring instrument; (iii) a laser light transmitter that emits visible laser light, the laser light transmitter being rotatable about a substantially vertical axis; and (iv) a first processing circuit, a first memory circuit, a first wireless communications circuit, and a first input/output interface circuit; (b) providing a remote controller, which includes: a second processing circuit, a second memory circuit, a second wireless communications circuit, a display, a user-controlled input circuit, and a second input/output interface circuit, wherein the laser controller and the remote controller communicate with one another by use of the first and second wireless communications circuits; (c) providing a movable target that is controlled by a human user; (d) placing the laser controller on a jobsite surface in a work area, and setting up the laser controller so that, in terms of jobsite coordinates, a position of the laser controller on the jobsite surface is determined; (e) executing a computer program using the remote controller, which displays a virtual jobsite illustration on the display; (f) selecting, using the display and the user-controlled input circuit, a specific point of interest on the virtual jobsite illustration, and virtually staking the specific point of interest on the virtual jobsite illustration; and (g) automatically indicating the specific physical point of interest to be staked: (i) by aiming the electronic distance measuring instrument of the laser controller directly at an azimuth angle of the specific point of interest on the jobsite surface; (ii) by aiming the laser light transmitter along the same azimuth angle as the electronic distance measuring instrument, thereby emitting a visible laser light line upon the jobsite surface that directly crosses the specific point of interest; and (iii) by the human user moving the movable target along the visible laser light line until the movable target is placed at the specific physical point of interest on the jobsite surface, as indicated by the electronic distance measuring instrument.

In accordance with still another aspect, a layout and point transfer system is provided, which comprises: (a) at least one laser controller, the at least one laser controller including: (i) a laser light transmitter that emits visible laser light, the laser light transmitter being rotatable about a substantially vertical axis; (ii) an electronic angle measuring instrument; and (iii) a first processing circuit, a first memory circuit, a first wireless communications circuit, and a first input/output interface circuit; and (b) a remote controller, which includes: a second processing circuit, a second memory circuit, a second wireless communications circuit, a display, a user-controlled input circuit, and a second input/output interface circuit, wherein the at least one laser controller and the remote controller communicate with one another by use of the first and second wireless communications circuits; wherein: (c) after the at least one laser controller is placed on a physical jobsite surface in a work area, the system is configured: (i) to set up the at least one laser controller so that, in terms of jobsite coordinates, a position of the at least one laser controller on the jobsite surface is determined; (ii) to execute a computer program using the remote controller, which displays a virtual jobsite illustration on the display; (iii) to select, using the display and the user-controlled input circuit, a specific point of interest on the virtual jobsite illustration; (iv) to virtually stake the specific point of interest on the virtual jobsite illustration; and (v) to automatically indicate, on the jobsite surface, the specific point of interest to be staked, by aiming the laser light transmitter of the at least one laser controller directly at an azimuth angle of the specific point of interest on the jobsite surface.

Still other advantages will become apparent to those skilled in this art from the following description and drawings wherein there is described and shown a preferred embodiment in one of the best modes contemplated for carrying out the technology. As will be realized, the technology disclosed herein is capable of other different embodiments, and its several details are capable of modification in various, obvious aspects all without departing from its principles. Accordingly, the drawings and descriptions will be regarded as illustrative in nature and not as restrictive.

BRIEF DESCRIPTION OF THE DRAWINGS

The accompanying drawings incorporated in and forming a part of the specification illustrate several aspects of the technology disclosed herein, and together with the description and claims serve to explain the principles of the technology. In the drawings:

DETAILED DESCRIPTION

Figure 1:
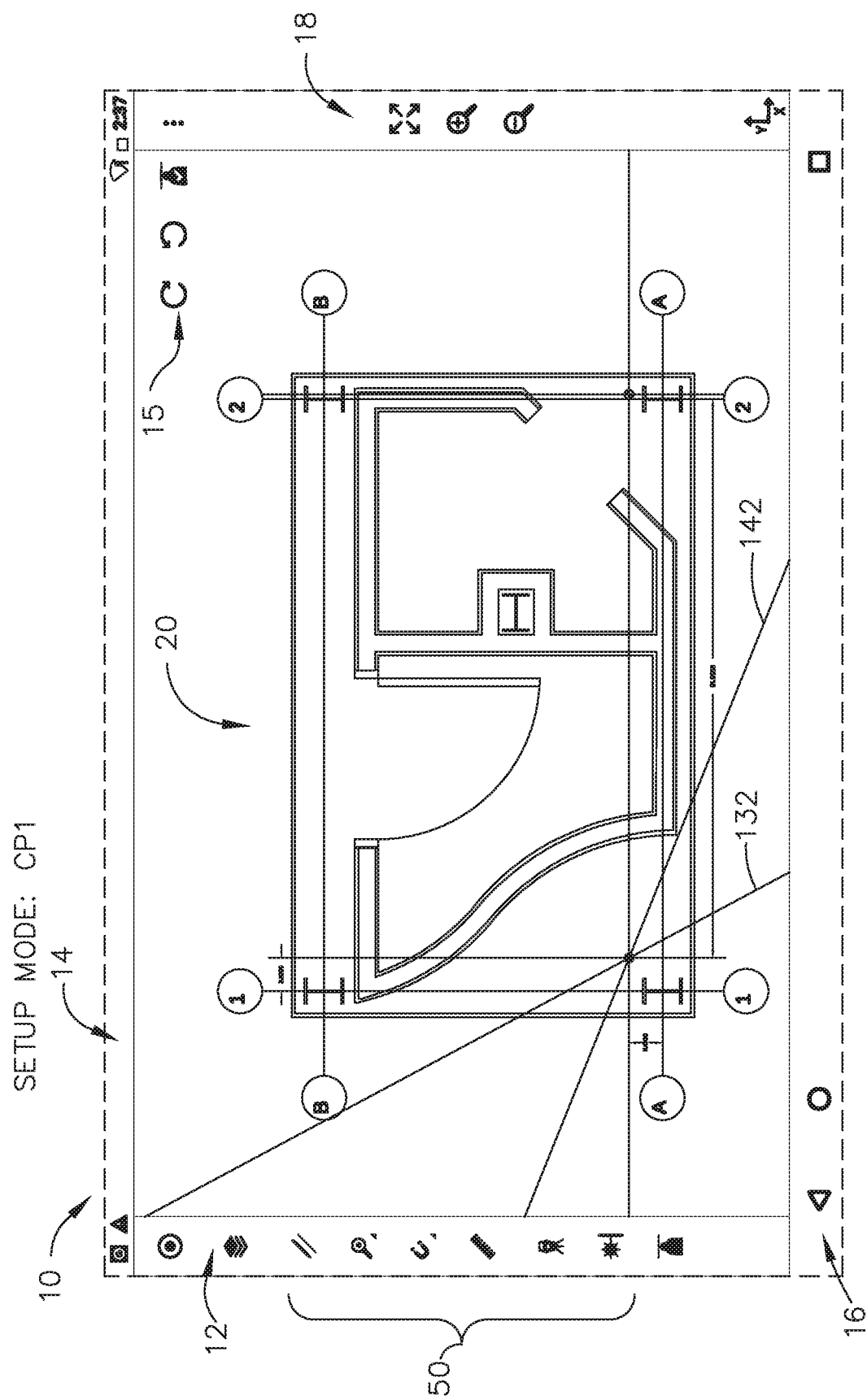
FIG. 1 is a diagrammatic view of a screen shot of a virtual jobsite illustration screen in the setup mode, used in a remote controller as constructed according to the principles of the technology disclosed herein. The laser light lines are illustrated as intersecting a first control point as part of the setup mode.

Reference will now be made in detail to the present preferred embodiment, an example of which is illustrated in the accompanying drawings, wherein like numerals indicate the same elements throughout the views.

It is to be understood that the technology disclosed herein is not limited in its application to the details of construction and the arrangement of components set forth in the following description or illustrated in the drawings. The technology disclosed herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings.

The terms "first" and "second" preceding an element name, e.g., first inlet, second inlet, etc., are used for identification purposes to distinguish between similar or related elements, results or concepts, and are not intended to necessarily imply order, nor are the terms "first" and "second" intended to preclude the inclusion of additional similar or related elements, results or concepts, unless otherwise indicated.

In addition, it should be understood that embodiments disclosed herein include both hardware and electronic components or modules that, for purposes of discussion, may be illustrated and described as if the majority of the components were implemented solely in hardware.

However, one of ordinary skill in the art, and based on a reading of this detailed description, would recognize that, in at least one embodiment, the electronic based aspects of the technology disclosed herein may be implemented in software. As such, it should be noted that a plurality of hardware and software-based devices, as well as a plurality of different structural components may be utilized to implement the technology disclosed herein. Furthermore, if software is utilized, then the processing circuit that executes such software can be of a general purpose computer, while fulfilling all the functions that otherwise might be executed by a special purpose computer that could be designed for specifically implementing this technology.

It will be understood that the term "circuit" as used herein can represent an actual electronic circuit, such as an integrated circuit chip (or a portion thereof), or it can represent a function that is performed by a "processing circuit," such as a microprocessor or an ASIC that includes a logic state machine or another form of processing element (including a sequential processing circuit). A specific type of circuit could be an analog circuit or a digital circuit of some type, although such a circuit possibly could be implemented in software by a logic state machine or a sequential processor. In other words, if a processing circuit is used to perform a desired function used in the technology disclosed herein (such as a demodulation function), then there might not be a specific "circuit" that could be called a "demodulation circuit;" however, there would be a demodulation "function" that is performed by the software. All of these possibilities are contemplated by the inventors, and are within the principles of the technology when discussing a "circuit."

The technology disclosed herein provides a computer software program that allows a CAD model file to be displayed as a virtual jobsite illustration (sometimes referred to herein as a "virtual jobsite illustration") on a remote controller display screen. Once the system is set up for a particular jobsite floor area, the software executes a "layout" mode that allows the user to both create and stake each point of interest sequentially, without the need to bounce back between two different modes of operation per point of interest. This new technology allows the user to identify an important location in the CAD model and immediately utilize that point of interest to tie the CAD model to the physical world. This approach eliminates the need to pre-create points in a CAD model, and therefore, reduces the necessary steps and the contractor's workflow on the jobsite floor. This system also allows the users to work more closely with the CAD model for determining important locations in the CAD model and quickly translating those locations into the physical world virtually simultaneously.

Figure 17:
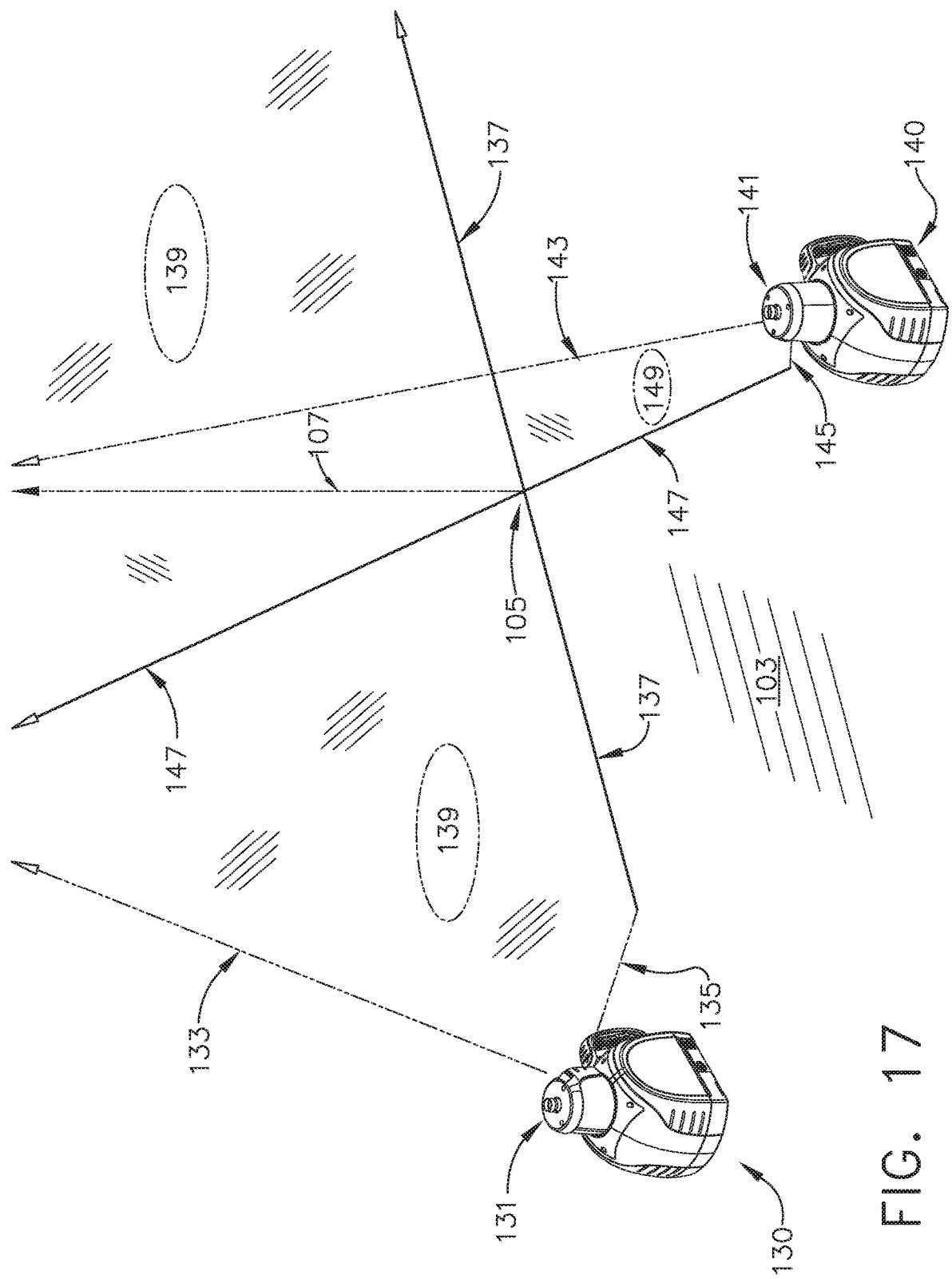
FIG. 17 is a perspective view showing a portion of a jobsite floor with two laser controllers producing vertical fan beams that intersect at a point of interest, as according to an operating sequence that uses the technology disclosed herein.

Referring briefly to FIG. 17, this figure illustrates a QuickMark Layout system, which is a construction layout system sold by Trimble Inc. of Sunnyvale, Calif. This system uses a mobile application (typically used on a tablet computer) and uses visible lasers that are on laser controllers, as seen on FIG. 17. In brief, the user loads a CAD model onto the mobile device (in which the CAD model is a virtual jobsite illustration), and the CAD model is opened and displayed by a QuickMark Layout application that runs on the remote controller. The user can then identify a point of interest in the CAD model by tapping the CAD geometry on the screen. The QuickMark Layout APP automatically corrects the user's tap to an exact location in the CAD model, such as the intersection of two lines. The user can tap a "create and stake" option, and a point then will be created at that location and the visible lasers will automatically be aimed at that point to visually locate the point with visible intersecting laser light lines on the physical jobsite floor. The user can immediately stake that physical point using the intersection of those visible laser light lines. It will be understood that the terms "stake," or "staking" a point of interest refers to the act of somehow physically marking a specific point on a jobsite floor—for example, an actual stake could be driven into the ground, or more likely (especially for indoor work on a concrete floor) a paint or chalk mark could be applied to the floor surface.

A sequence of operation will now be presented showing how the technology disclosed herein can be used in detailed steps. The operating software is used on a tablet computer and is generically known as the QuickMark Layout system, and is also known as the Tap 'n Go interior layout system, which is sold by Trimble Inc. of Sunnyvale, Calif. This sequence of operation is presented below in outline form, which is referred to as OUTLINE #2.

OUTLINE #2—SEQUENCE OF OPERATION, using a Spectra Model QML800 QuickMark Layout system; also known as the Tap 'n Go Interior Layout System; sold by Trimble, Inc. of Sunnyvale, Calif.

(A) On the remote controller: select and display a CAD model file of a virtual jobsite illustration.

(B) User selects the START LAYOUT function.

(C) User selects the START LASER ALIGNMENT function.

(C-1) This creates an alignment axis between the two laser controllers.

(D) User selects the SETUP CONTROL POINTS function.

(D-1) The laser transmitters are rotated until they are both physically aimed at CP1.

(D-2) This occurs under the user's control, using the remote controller to send commands.

(E) User selects the SAVE CONTROL POINT function.

(E-1) User now views the CAD model on the remote controller screen.

(E-2) User "taps" the screen at the correct point of the CAD model.

(E-3) The remote controller screen now displays a "point icon" (a colored circle).

(E-4) The remote controller screen now displays a small menu box of choices.

(E-5) The user "taps" the screen to confirm that point.

(E-6) The system software automatically gives that point a designation, such as "p3".

(E-7) The remote controller shows the laser light lines on the screen, intersecting at "p3".

(This may be an approximation at this time, because setup is not yet complete.)

(E-8) The user selects the SAVE function; point "p3" becomes the first control point.

(F) Still under the SETUP CONTROL POINTS function:

(F-1) The laser transmitters are rotated until they are both physically aimed at CP2.

(F-2) This occurs under the user's control, using the remote controller to send commands.

(G) User again selects the SAVE CONTROL POINT function.

(G-1) User now views the CAD model on the remote controller screen.

(G-2) User "taps" the screen at the correct point of the CAD model.

(G-3) The remote controller screen now displays a "point icon" (a colored circle).

(G-4) The remote controller screen now displays a small menu box of choices.

(G-5) The user "taps" the screen to confirm that point.

(G-6) The system software automatically gives that point a designation, such as "p4". (G-7) The remote controller shows the laser light lines on the screen, intersecting at "p4".

(This may be an approximation at this time, because setup is not yet complete.)

(G-8) The user selects the SAVE function; point "p4" becomes the second control point.

(H) The user selects the CONTINUE function; setup is finished.
- (H-1) The system software now automatically advances to the "LAYOUT" mode.
- (H-2) The remote controller screen displays the virtual jobsite illustration, now having been set up.

(I) The user decides on a first point of interest (point "n") to be laid out.
- (I-1) User views the CAD model on the remote controller screen.
- (I-2) User "taps" the screen at the correct point of the CAD model.
- (I-3) The remote controller screen now displays a "point icon" (a colored circle).
- (I-4) The remote controller screen now displays a small menu box of choices.
  - (I-4a) There are three options, displayed as icons:
  - (I-4b) CREATE.
  - (I-4c) CREATE & STAKE.
  - (I-4d) CANCEL.
- (I-5) The user "taps" the screen at the CREATE & STAKE icon to confirm that point.
- (I-6) The system software automatically gives that point a designation, such as "p9".
- (I-7) The laser transmitters are rotated until they are both physically aimed at point "p9".
  - (I-7a) This occurs automatically, using jobsite coordinates provided by the virtual jobsite illustration that is being used by the remote controller.
- (I-8) The remote controller shows the laser light lines on the screen, intersecting at "p9".
- (I-9) Once the two laser controllers stop rotating the laser transmitters:
  - (I-9a) The crossing point (the "X") of the actual laser light lines visually indicates where the physical point is located on the jobsite floor.
  - (I-9b) The user now moves to that crossing point and stakes it on the jobsite floor.
- (I-10) The user selects the SAVE function; point "p9" becomes the first point of interest to be staked during this layout session at the jobsite.

(J) The user decides on a second point of interest (point "n+1") to be laid out.
- (J-1) User views the CAD model on the remote controller screen.
- (J-2) User "taps" the screen at the correct point of the CAD model.
- (J-3) The remote controller screen now displays a "point icon" (a colored circle).
- (J-4) The remote controller screen now displays a small menu box of choices.
  - (J-4a) There are three options, displayed as icons:
  - (J-4b) CREATE.
  - (J-4c) CREATE & STAKE.
  - (J-4d) CANCEL.
- (J-5) The user "taps" the screen at the CREATE & STAKE icon to confirm that point.
- (J-6) The system software automatically gives that point a designation, such as "p10".
- (J-7) The laser transmitters are rotated until they are both physically aimed at point "p10".
  - (J-7a) This occurs automatically, using jobsite coordinates provided by the virtual jobsite illustration that is being used by the remote controller.
- (J-8) The remote controller shows the laser light lines on the screen, intersecting at "p10".
- (J-9) Once the two laser controllers stop rotating the laser transmitters:
  - (J-9a) The crossing point (the "X") of the actual laser light lines visually indicates where the physical point is located on the jobsite floor.
  - (J-9b) The user now moves to that crossing point and stakes it on the jobsite floor.
- (J-10) The user selects the SAVE function; point "p10" becomes the second point of interest to be staked during this layout session at the jobsite.

(K) The user decides on a "next" point of interest (point "n+m") to be laid out.
- (K-1) User views the CAD model on the remote controller screen.
- (K-2) User "taps" the screen at the correct point of the CAD model.
- (K-3) The remote controller screen now displays a "point icon" (a colored circle).
- (K-4) The remote controller screen now displays a small menu box of choices.
  - (K-4a) There are three options, displayed as icons:
  - (K-4b) CREATE.
  - (K-4c) CREATE & STAKE.
  - (K-4d) CANCEL.
- (K-5) The user "taps" the screen at the CREATE & STAKE icon to confirm that point.
- (K-6) The system software automatically gives that point a designation, such as "p+q".
- (K-7) The laser transmitters are rotated until they are both physically aimed at point "p+q".
  - (K-7a) This occurs automatically, using jobsite coordinates provided by the virtual jobsite illustration that is being used by the remote controller.
- (K-8) The remote controller shows the laser light lines on the screen, intersecting at "p+q".
- (K-9) Once the two laser controllers stop rotating the laser transmitters:
  - (K-9a) The crossing point (the "X") of the actual laser light lines visually indicates where the physical point is located on the jobsite floor.
  - (K-9b) The user now moves to that crossing point and stakes it on the jobsite floor.
- (K-10) The user selects the SAVE function; point "p+q" becomes the n+mth point of interest to be staked during this layout session at the jobsite.

(L) The procedure of steps (K) through (K-10) continues with additional layouts and stakes, until the end of this layout session at the jobsite.

Referring now to FIG. 1, a screenshot of the visual display of a remote controller (which is described in detail referring to FIG. 15) is illustrated, generally designated by the reference numeral 10. This screenshot depicts a room of an architect virtual jobsite illustration, in which the room has a certain pattern of walls and other physical items; the overall room is generally designated by the reference numeral 20. The operating software provides several menu icons in groups along the borders, such as a series of icons along the left border 12, a top menu border 14, a bottom border 16, and a right-hand border 18. In addition, there are some further icons at the reference numeral 15 that are not necessarily inside the menu selection borders. The different icons allow the user to select various functions in the QuickMark Layout system operating software that runs as an APP on the tablet computer.

On FIG. 1, there are two slanted lines at 132 and 142 which represent the laser light lines being generated by the laser transmitters on the two laser controllers 130 and 140, as viewed on FIG. 17. These laser lines are illustrated as intersecting at a particular point, which on FIG. 1 represents the first control point that will be used during a setup mode. The display of FIG. 1 is titled "SETUP MODE: CP1." This particular display sequence is designated #50 along the left-hand side, indicating that this is the first sequential display of this procedure. The next sequential display will be designated #51, for example. This display sequence #50 specifically refers to step "E-7" on OUTLINE #2, presented above.

Figure 2:
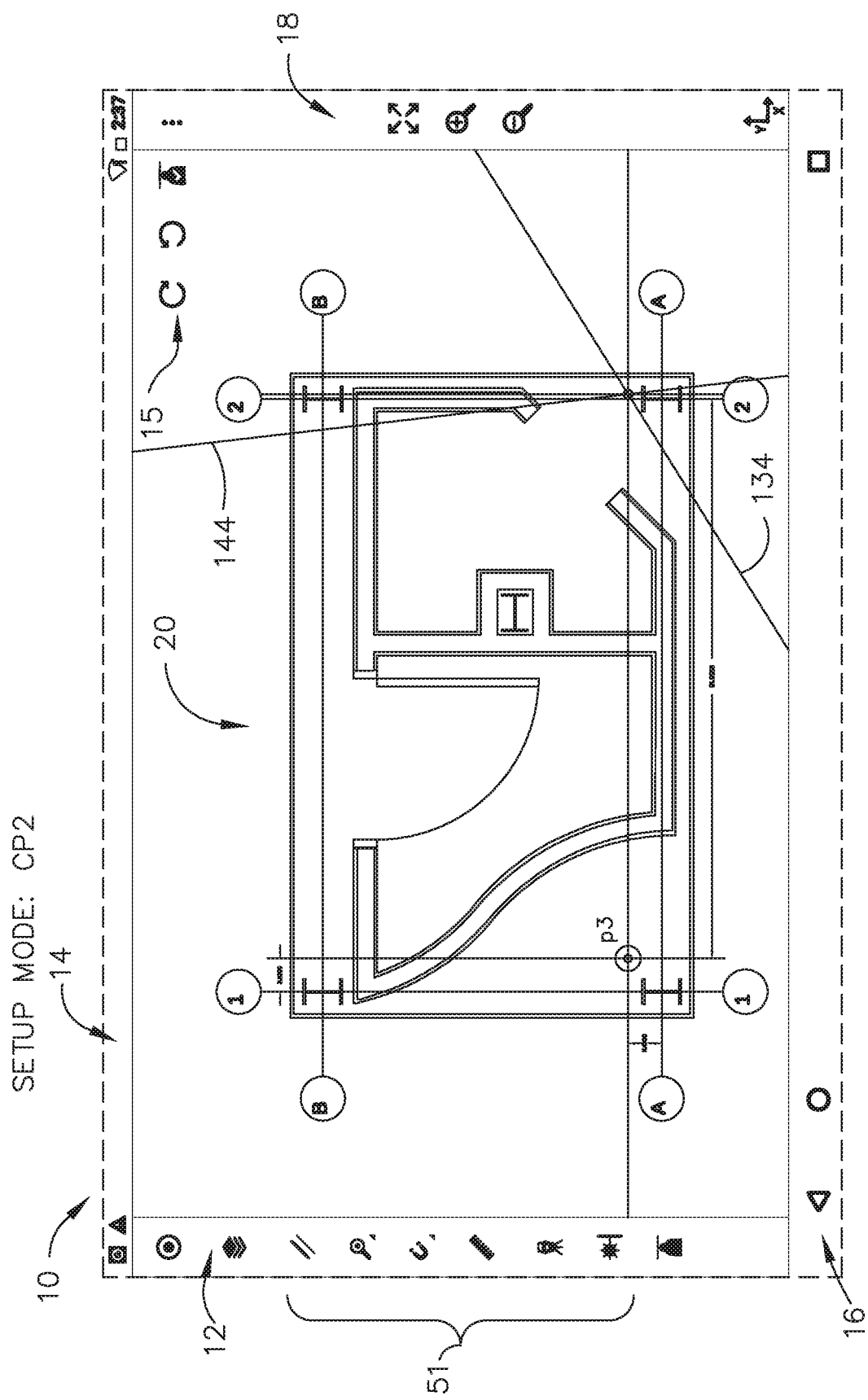
FIG. 2 is a diagrammatic view of a screen shot showing a second control point being selected as part of the setup mode of the system using the remote controller of FIG. 1.

Referring now to FIG. 2, the same type of display is again illustrated, but this time representations of the laser light lines are pointing at a different placement on the architect file (the CAD model) depicted on the remote controller's display screen. The same overall menu bars are available, and the overall room is once again displayed, as designated by the reference numeral 20. This display is sequentially numbered #51, indicating the next step in the procedure. Representations of the laser light lines are designated 134 and 144, and are pointing at a second control point, which is required as part of the setup mode. This display is titled "SETUP MODE: CP2." This particular display (or screenshot) corresponds to step "G-7" in the OUTLINE #2, presented above.

Since the first control point has already been established by the time the user arrives at the display sequence #51, the point designation "p3" is visible at the first control point location, which was selected in the previous step showing the display designation #50 (which is FIG. 1). This point also exhibits a pair of concentric circles, so the user can visibly see that this particular point "p3" has been saved as a control point (which occurred in step "E-8" in OUTLINE #2, above).

Figure 3:
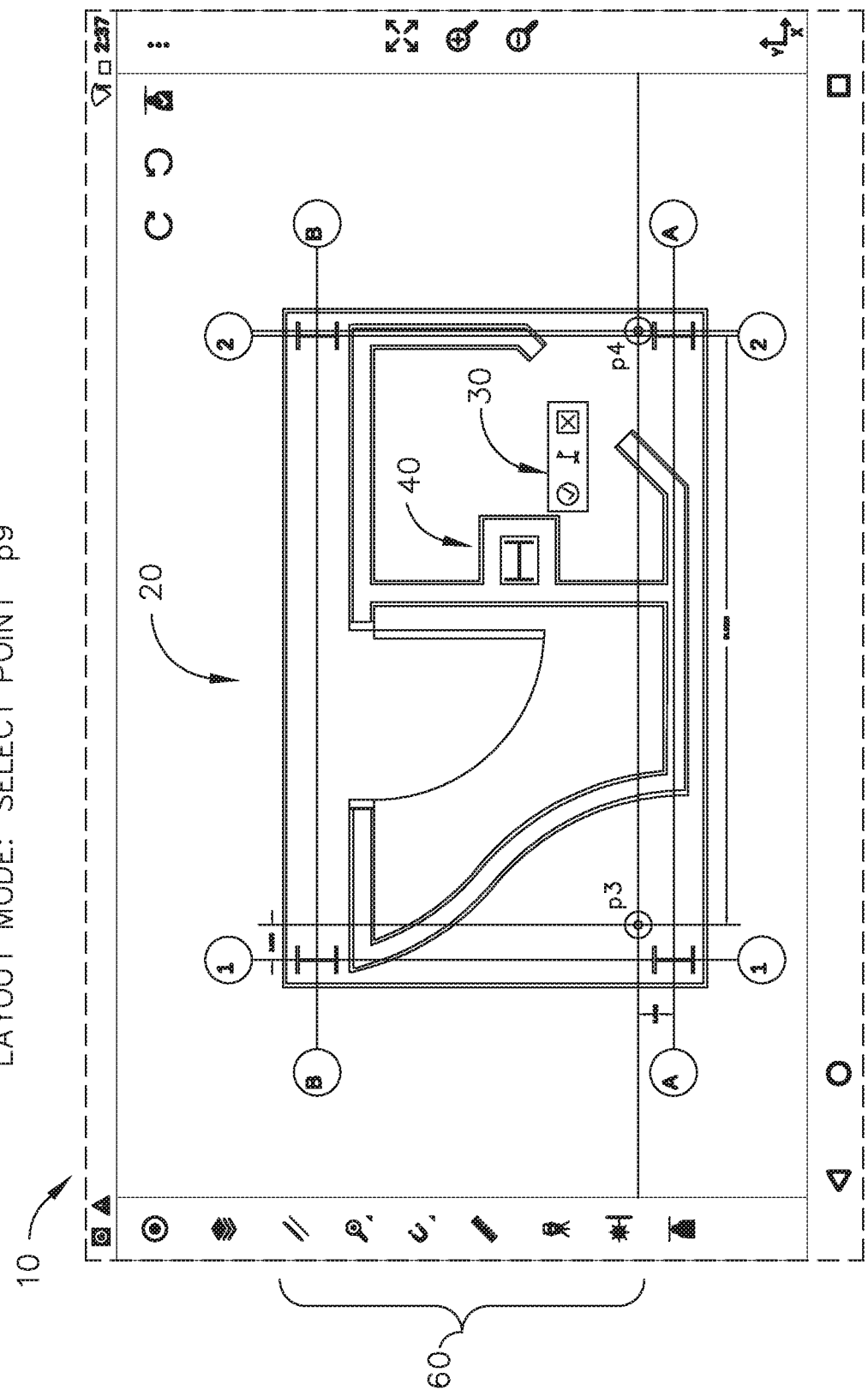
FIG. 3 is a diagrammatic view of a screen shot showing the user selecting a point of interest in the layout mode.

After the step "G-8" occurs in the sequence of OUTLINE #2, a point "p4" will become the second control point saved in the system software. A pair of concentric circles will become visible on the screen of the remote controller, along with the point designation Referring now to FIG. 3, the same overall room of the virtual jobsite illustration is again displayed, designated by reference numeral 20. The title of this figure is "LAYOUT MODE: SELECT POINT "p9". The user is about to work in a central area of the display that shows an enclosed I-beam, which (as an overall structure) is designated by the reference numeral 40 on FIG. 3. This figure is also labeled by the sequential designator #60, which is the next major step in the overall sequence of operation in this example. In FIG. 3, the user has "tapped" the screen at a point near the bottom right-hand corner of the enclosed I-beam, and the remote controller screen now displays a small menu box of choices, which are designated by the reference numeral 30 on FIG. 3. In this example of the operating system software, the user has three possible choices at this time: the first choice is "CREATE," the second choice is "CREATE & STAKE," and the third choice is "CANCEL." Before the user selects one of these three options, this display corresponds to step "I-4" on the OUTLINE #2, presented above.

To use the more automated features of this new operating software system, the user will select the "CREATE & STAKE" option, and the system software will now automatically label that position with a new point designation, such as "p9." A pair of concentric circles will also appear, once that point is saved. After the CREATE & STAKE icon has been tapped on the screen of the remote controller, both laser transmitters are rotated until they both are aimed at that physical point "p9". This provides the user with a visible set of laser light lines on the jobsite floor that cross at the exact point of interest that is to be staked. In other words, the physical point "p9" will visibly "appear" on the jobsite floor at the "X" where the laser light lines actually intersect on the jobsite floor.

Figure 4:
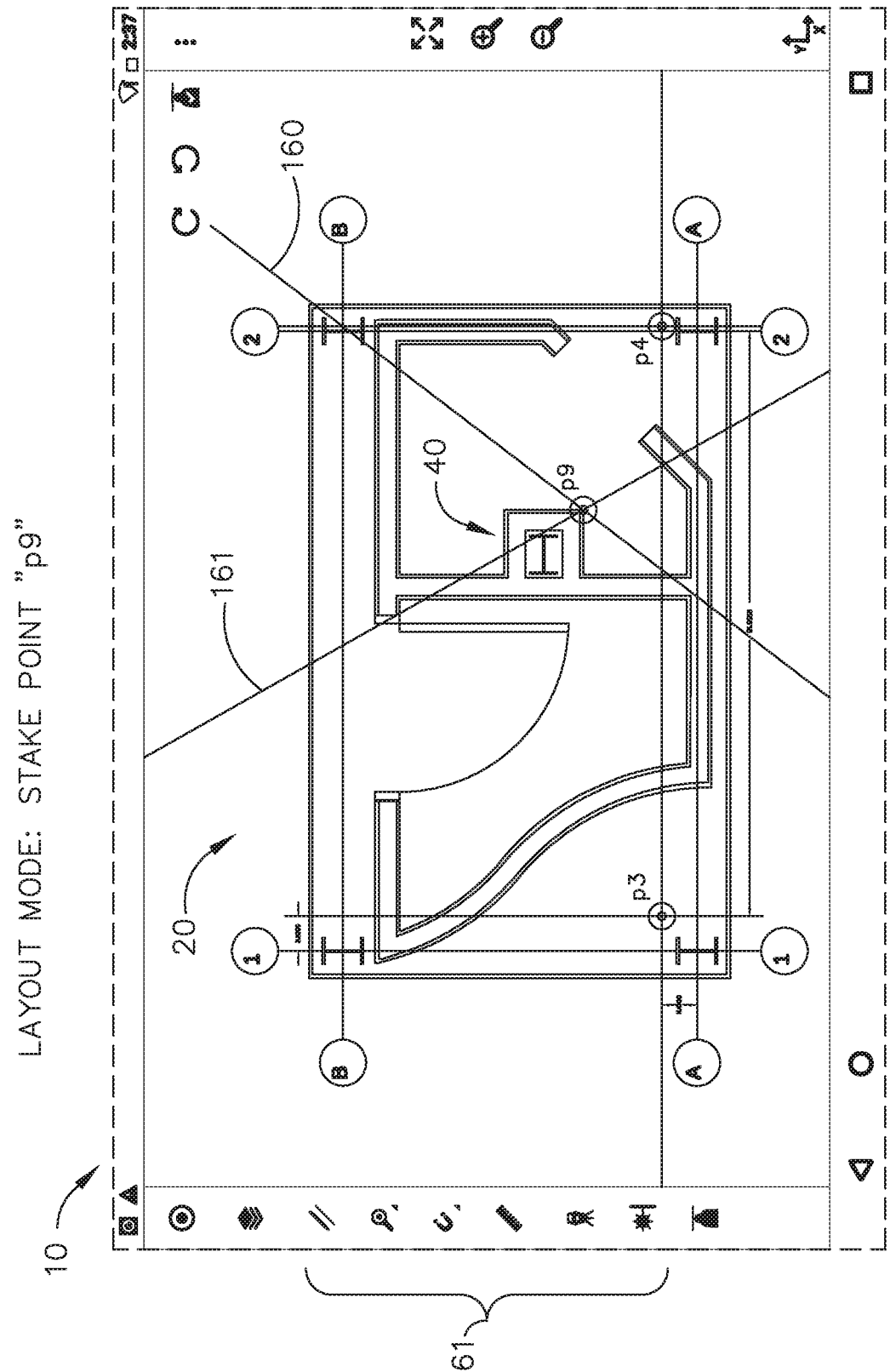
FIG. 4 is a diagrammatic view of a screen shot showing the user staking that first point of interest in the layout mode.

Referring now to FIG. 4, the situation is illustrated in which the representations of laser light lines 161 and 160 intersect at that exact point that is now designated p9. This display is referred to as the "LAYOUT MODE: STAKE POINT "p9", and this display has a numerical sequence designator #61. The screenshot depicted in FIG. 4 corresponds to the step "I-10" on OUTLINE #2, presented above.

As noted above, a user will often want to magnify (or "zoom in" on) the display to be certain of selecting the precise correct point on the CAD model appearing on the screen on the remote controller. Therefore, FIGS. 5 and 6 are provided to show the sequential screens #60 and #61 all over again, but showing a magnified view which would typically be used on the jobsite by a user of this point layout system.

Figure 5:
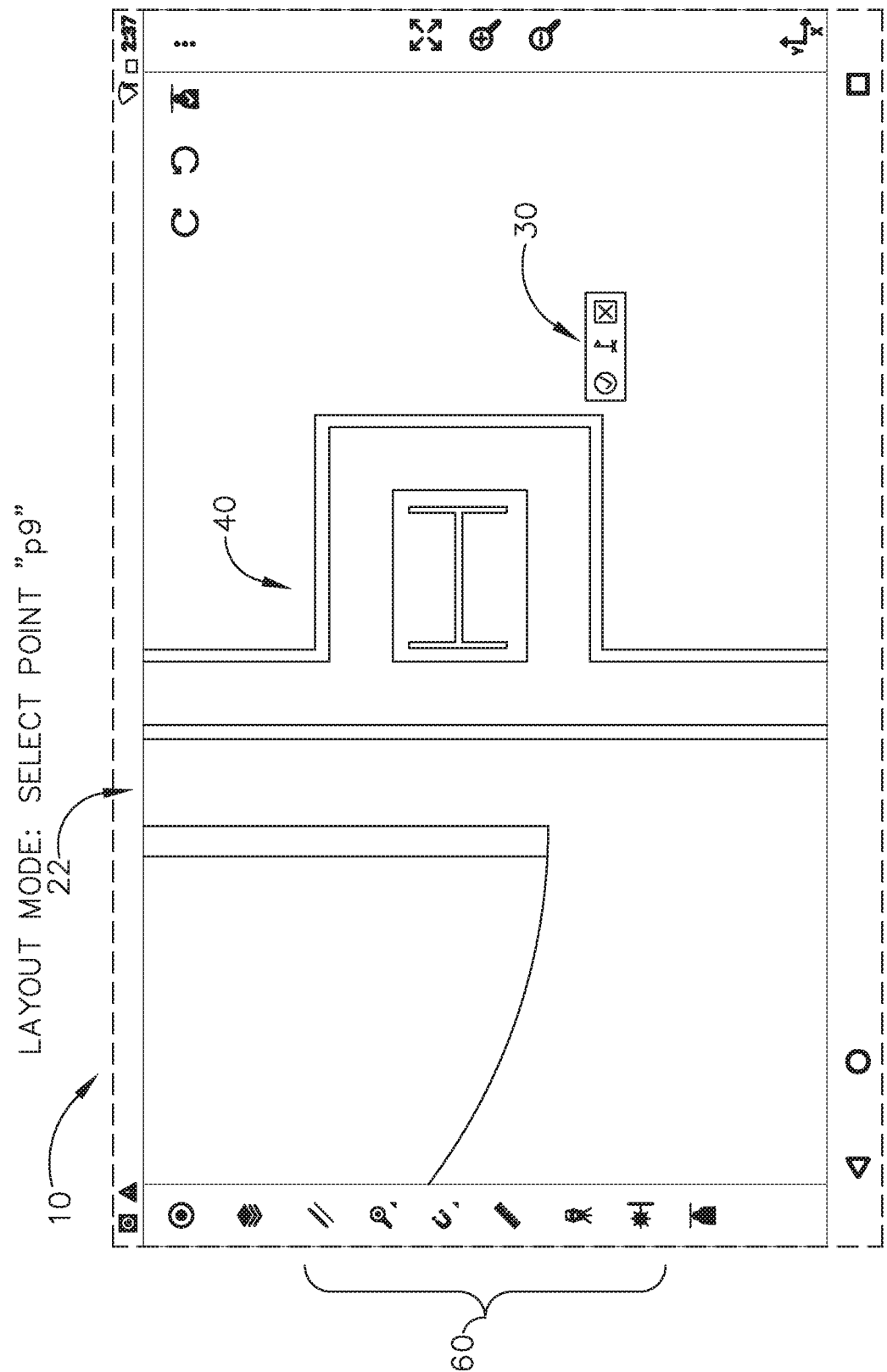
FIG. 5 is a diagrammatic view of a screen shot showing the user selecting a point of interest in the layout mode, showing the screen shot of FIG. 3 in a magnified view.
Figure 6:
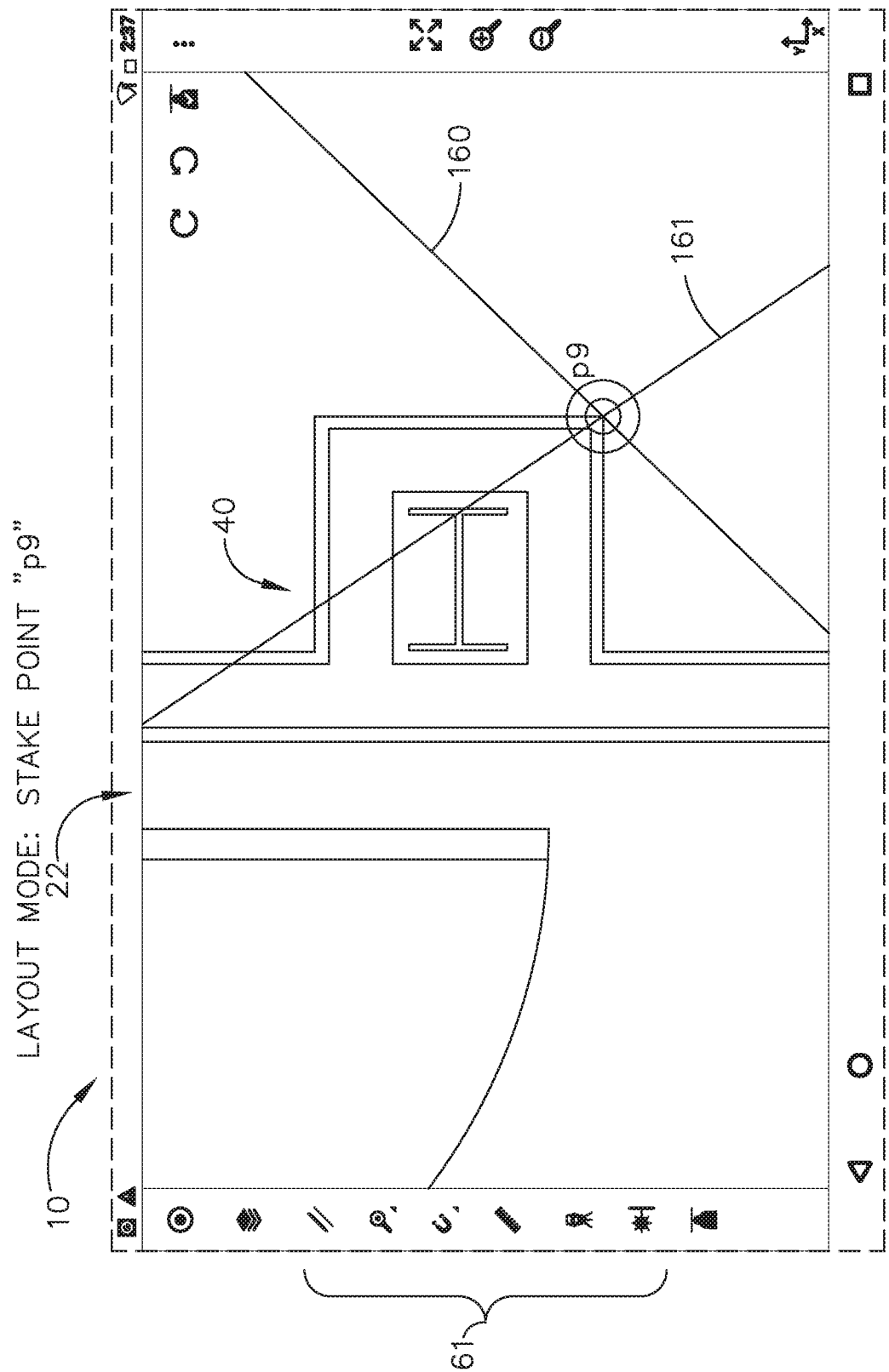
FIG. 6 is a diagrammatic view of a screen shot showing the user staking that first point of interest in the layout mode, showing the screen shot of FIG. 4 in a magnified view.

Referring now to FIG. 5, the entire room of the architect virtual jobsite illustration is no longer visible, and instead only the enclosed I-beam portion is seen, as designated by the reference numeral 40. The title of FIG. 5 is the same as that as FIG. 3:

"LAYOUT MODE: SELECT POINT "p9".

In this view, the overall display is only a portion of the room that was displayed in the earlier figures, and this portion is now designated by the reference numeral 22. This is the same sequential step #60 that was seen in FIG. 3, and the same small icon box of optional choices is again presented, as indicated by the reference numeral 30. Here it can be seen that the user can more easily select the precise intersection of the exact desired lines at the lower right-hand corner of the wall that encloses the I-beam.

It should be noted that, if the user accidently taps at the wrong spot on the display screen of the remote controller, a temporary dot will be placed at the point on the screen that the operating software "believes" was the correct point. If it turns out that the point now being displayed is not the correct point (i.e., it was not the intended point to be selected insofar as the user was concerned), then the user can quickly hit the CANCEL option on the three-icon box 30, and then quickly try to select the correct point once again. If necessary, the user can magnify the screen to a larger extent so as to more easily eliminate incorrect choices if they keep occurring.

Referring now to FIG. 6, this is the same screen sequence #61 as was seen on FIG. 4, except that the screen has been magnified so the user can more easily "tap" at the correct point that is to be laid out. The title of this screen is "LAYOUT MODE: STAKE POINT "p9". On this screen at FIG. 6, the concentric circles are larger, and also can be colored in, if desired. They also show the point designator "p9," as before.

Figure 7:
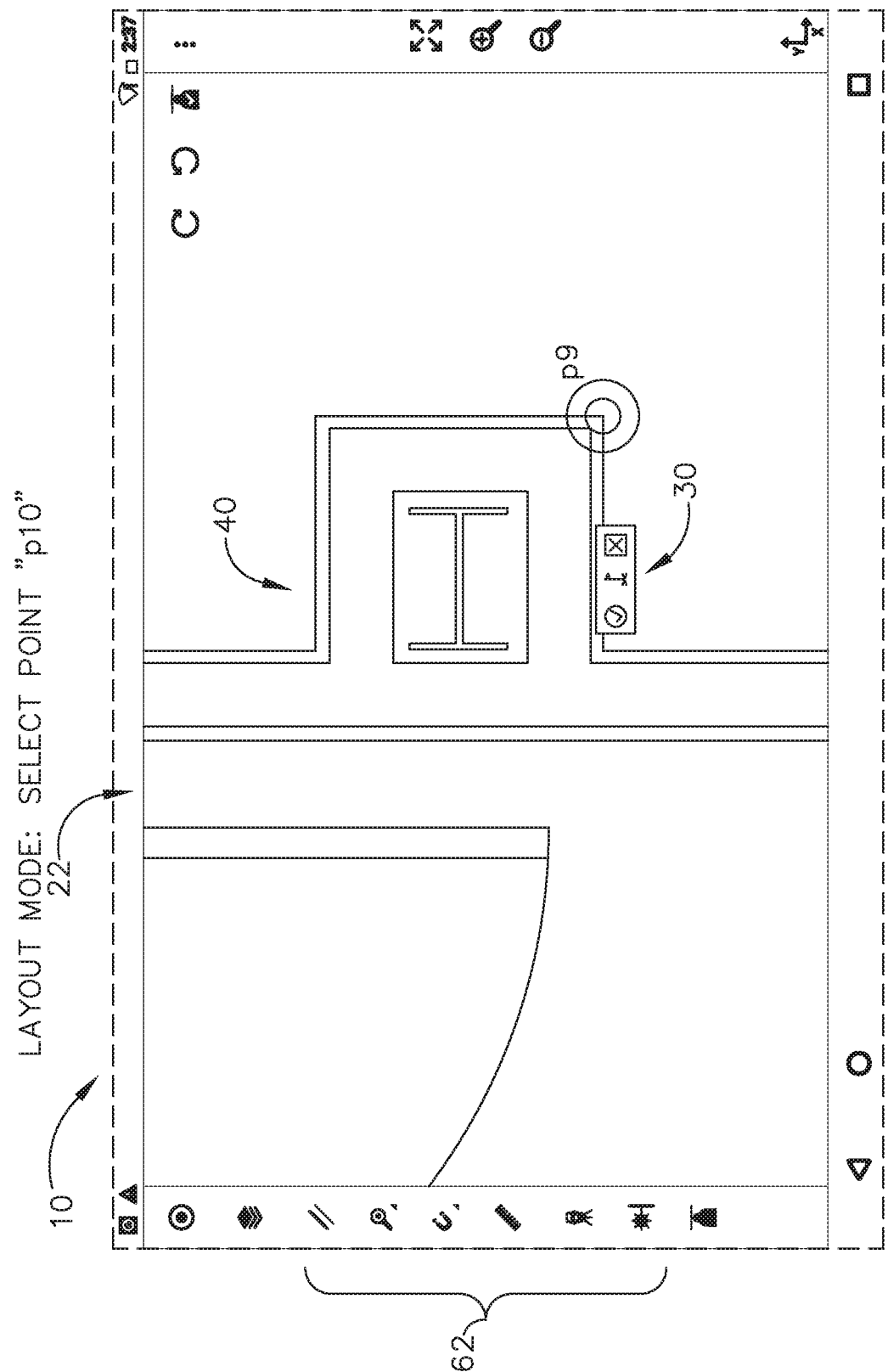
FIG. 7 is a diagrammatic view of a screen shot in which the user is selecting a second point of interest in the layout mode.

Referring now to FIG. 7, now that point "p9" has been laid out and staked, the user may move on to the next point of interest. The title of FIG. 7 is "LAYOUT MODE: SELECT POINT "p10." The user again taps at the correct location on the screen of the remote controller, and when that occurs the three-icon box 30 appears once again. This is the next major step in the sequence of operation, and this display designator is #62 to show that status. This screenshot of FIG. 7 corresponds to the step "J-4" of the OUTLINE #2, presented above.

Figure 8:
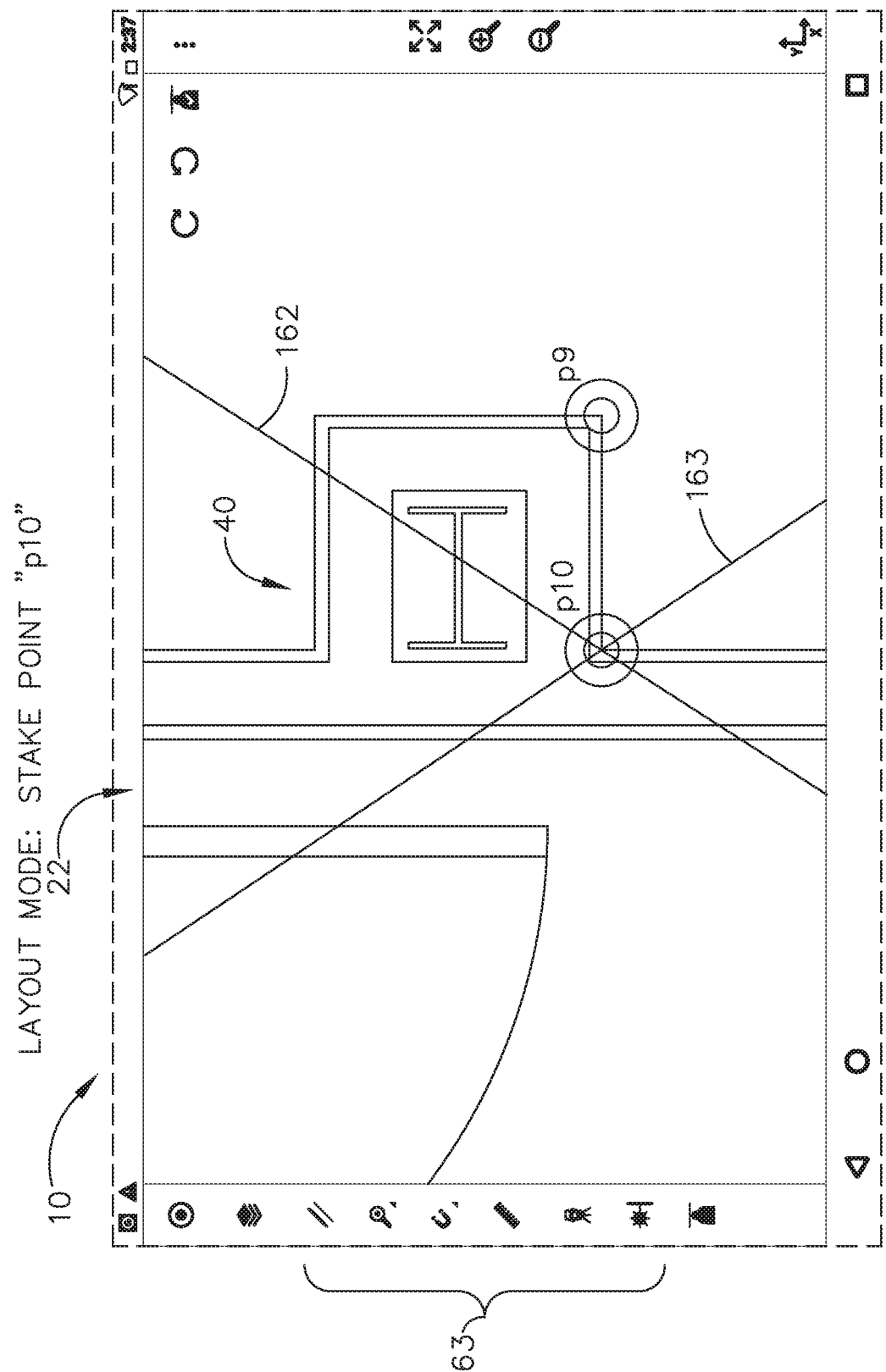
FIG. 8 is a diagrammatic view of a screen shot in which the user is staking a second point of interest in the layout mode.

Referring now to FIG. 8, the user has tapped the "CREATE & STAKE" icon to confirm the point "p10", and the two laser controllers will now both automatically aim their laser fan beams at the physical point p10 on the jobsite floor. This will visually show the user the exact location (with intersecting laser light lines) as to where the physical point p10 is located and should be staked. Once all that occurs, representations of laser light lines 162 and 163 will show up on the screen, as seen in FIG. 8, as intersecting at that point p10. This is this screen sequence #63. The title of FIG. 8 is "LAYOUT MODE: STAKE POINT "p10". The screenshot of FIG. 8 corresponds to the step "J-10" on the OUTLINE #2, above.

Figure 9:
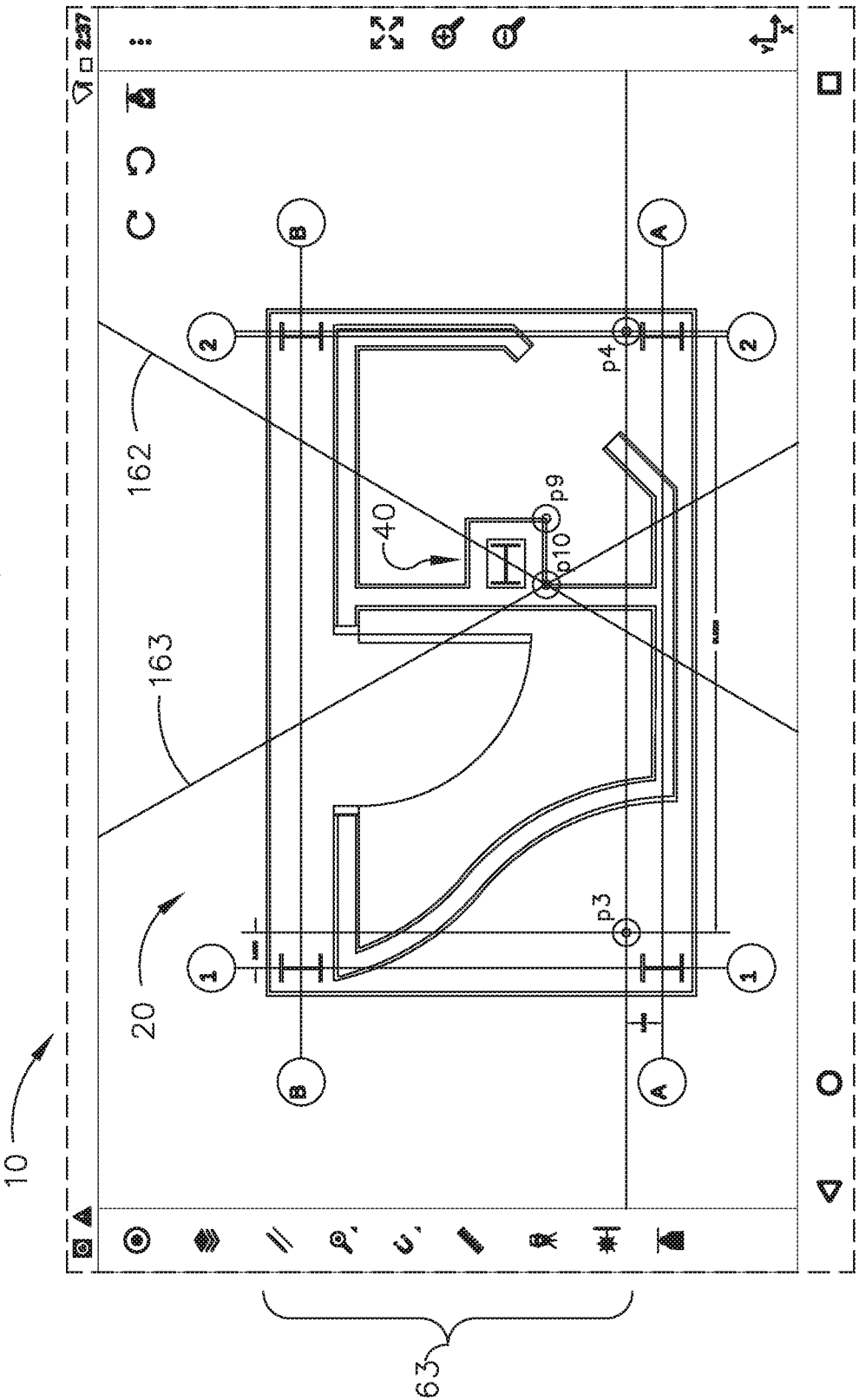
FIG. 9 is a diagrammatic view of a screen shot in which the user is staking a second point of interest in the layout mode, in which the screen shot shows the entire room in a non-magnified view.

Referring now to FIG. 9, this screenshot shows the same exact status as that of FIG. 8, hence the numeric sequence designation #63 along the left-hand side of the view. However, the user has now zoomed out to see the entire room of this virtual jobsite illustration, once again. The staked points "p9" and "p10" are both visible, and representations of the laser light lines 162 and 163 are still intersecting at the point "p10".

The user can now move on to a different portion of the physical room to lay out points that were not viewable in the zoomed-in views such as FIG. 8. This is still the step J-10, in the OUTLINE #2 above.

Figure 10:
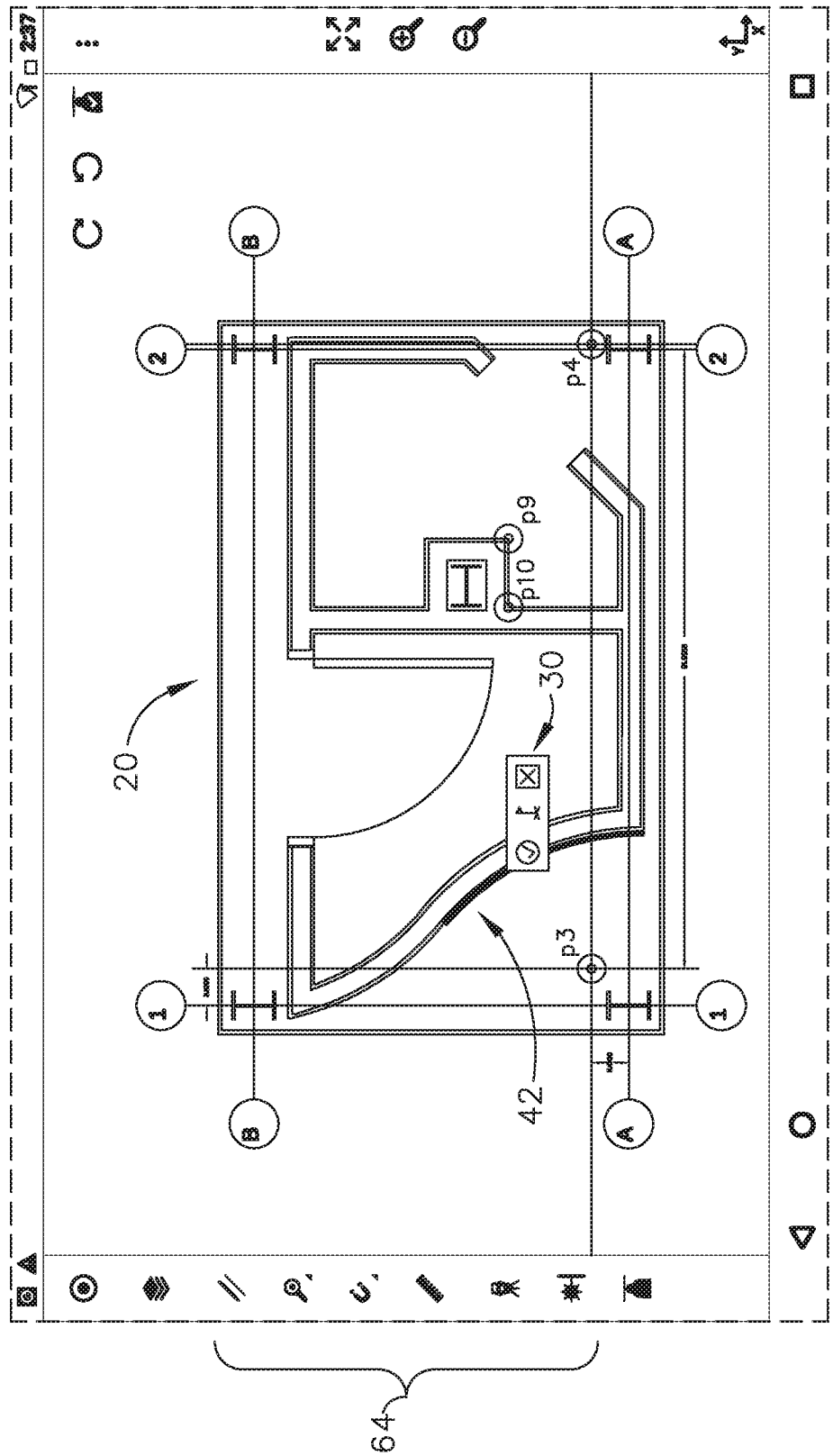
FIG. 10 is a diagrammatic view of a screen shot showing the user selecting an arc in the layout mode.

Referring now to FIG. 10, the user has moved on so as to select a point along an arc 42. Once the user has selected one of the points along that arc, the small icon box with the three options appears once again, as at reference numeral 30. This figure is titled "LAYOUT MODE: SELECT ARC "a1". This screenshot is designated #64 in the sequence of operations for this description. As can be seen on FIG. 10, the previously selected points of interest p9 and p10 are shown as having been staked on the virtual jobsite illustration. This display of FIG. 10 corresponds to step "K-4" in OUTLINE #2, presented above.

Figure 11:
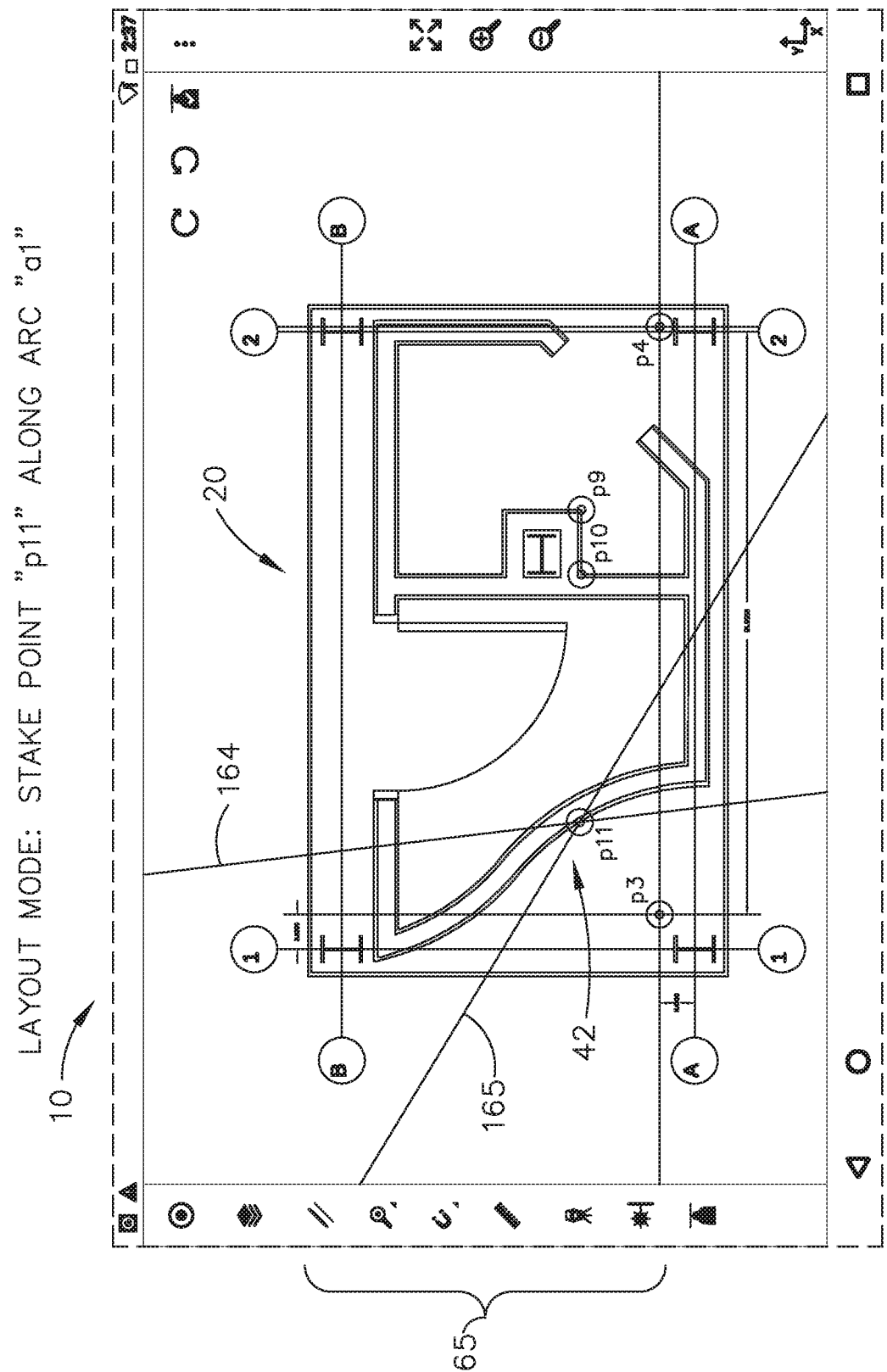
FIG. 11 is a diagrammatic view showing a screen shot of the user staking a point along the arc of FIG. 10.

Referring now to FIG. 11, this display is titled "LAYOUT MODE: STAKE POINT "p11" ALONG ARC "a1." To arrive at FIG. 11, the user selected the "CREATE & STAKE" option at the three-option box 30 on FIG. 10. Once that occurred, the two laser transmitters are automatically aimed so that their laser light lines will cross exactly at the physical point of interest that will become "p11." Representations of these laser light lines are visible on the screenshot of FIG. 11, as designated by the lines 164 and 165. These laser light lines actually exist on the physical jobsite floor and their crossing point will show the user exactly where the physical point of interest should be staked. This is screen sequence #65 in this example, and corresponds to step "K-10" in OUTLINE #2, above.

Figure 12:
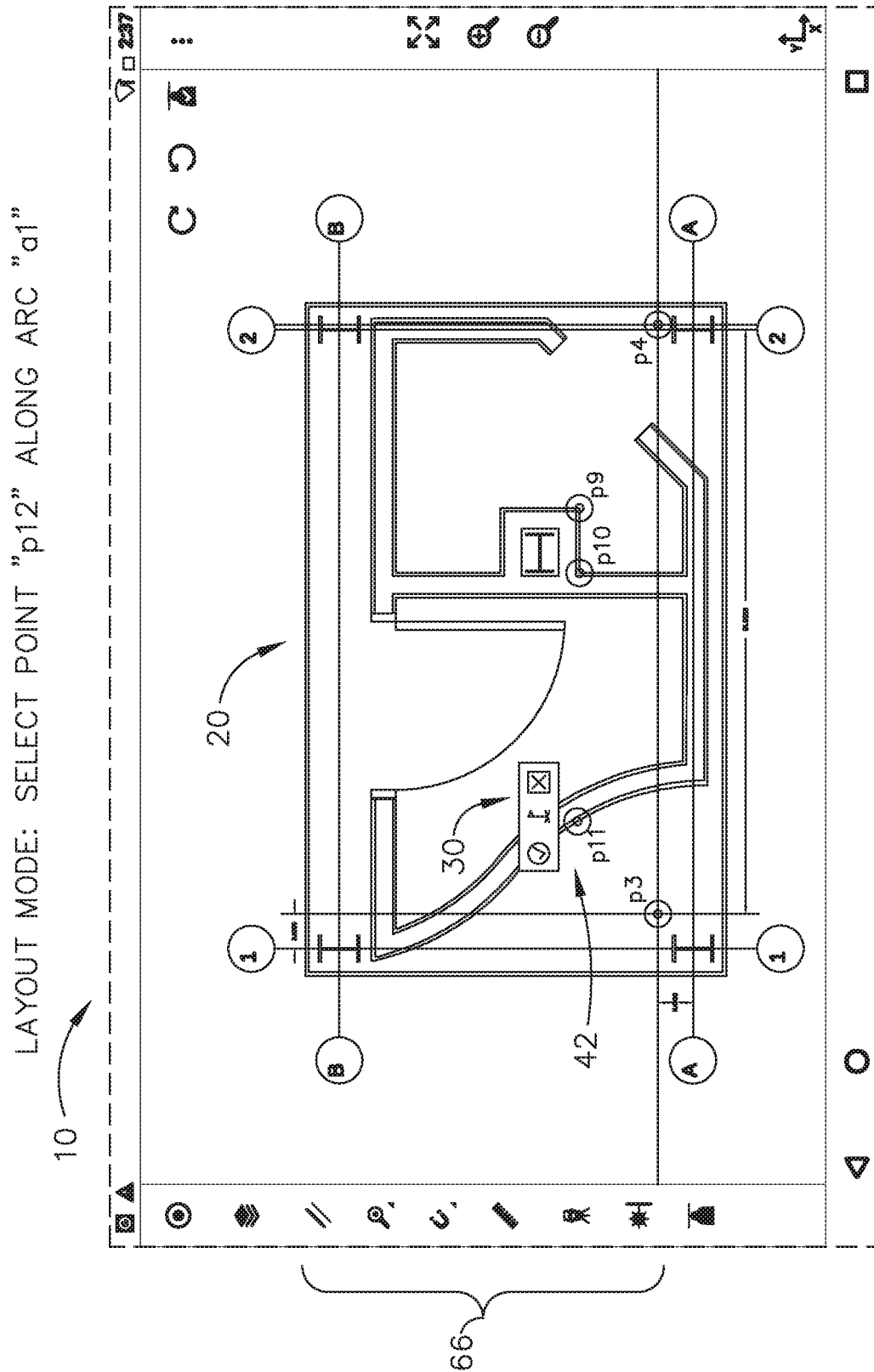
FIG. 12 is a diagrammatic view showing a screen shot of the user selecting a second point along the arc of FIG. 10.
Figure 13:
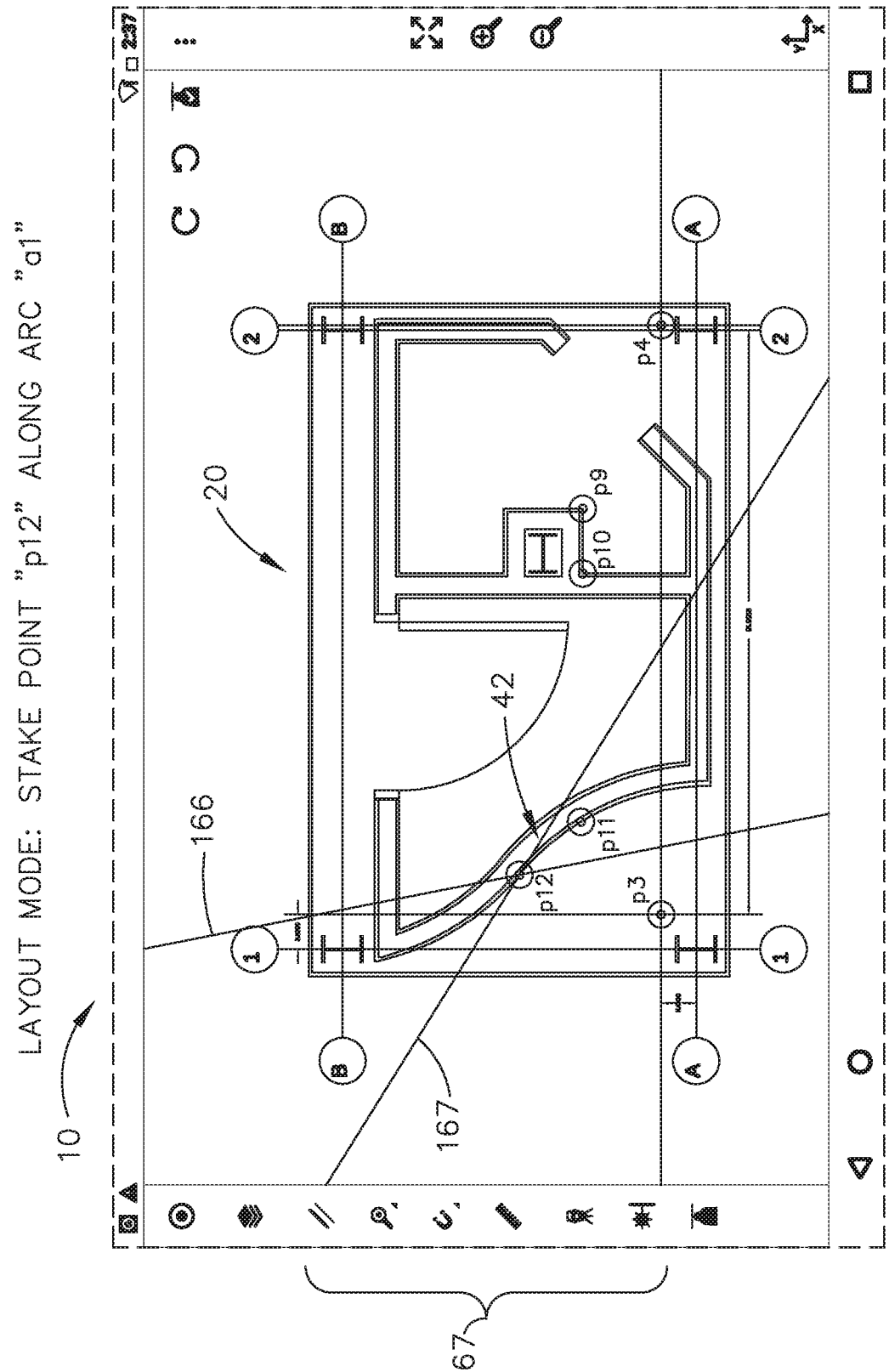
FIG. 13 is a diagrammatic view showing a screen shot of the user staking a second point along the arc of FIG. 10.

To provide one more example, FIGS. 12 and 13 will show yet another point of interest to be selected and staked. Referring now to FIG. 12, the point p11 has been staked along the arc 42, and the icon showing that status is visible on this screenshot. The user has selected yet another point along the arc 42, and therefore, the small menu box of three choices is once again displayed at 30. This is display sequence #66 in this example. With regard to the step number in OUTLINE #2, the operational sequence is back at step K-4.

Referring now to FIG. 13, the user has selected the "CREATE & STAKE" option from the three-icon option box 30, and the point "p12" has been selected by the user tapping on the monitor screen of the remote controller. The two laser transmitters are now automatically rotated so that their laser light lines cross at the physical jobsite floor location where point p12 is physically positioned. Representations of these laser light lines 166 and 167 also appear on the screenshot of FIG. 13. The title of FIG. 13 is "LAYOUT MODE: STAKE POINT "p12" ALONG ARC "a1." This is screen designation #67 in the sequence of operational steps of this example. The user can now walk to that point and easily see exactly where the point p12 is physically located so as to be properly staked. This corresponds to step K-10 in the OUTLINE #2, above.

Figure 14:
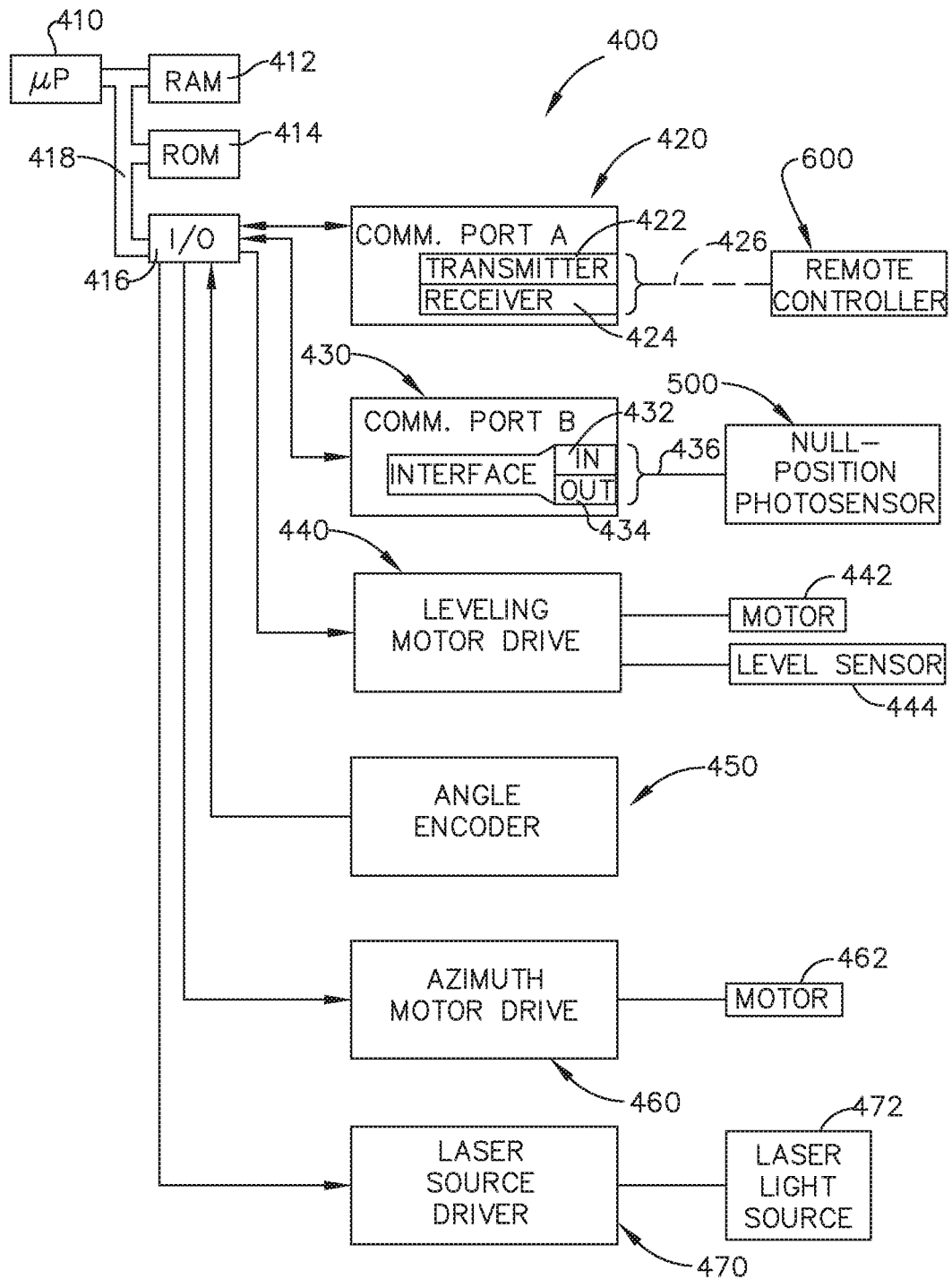
FIG. 14 is a block diagram of the major components of a laser controller that is used in the technology disclosed herein, as constructed according to the principles of the technology disclosed herein.

Referring now to FIG. 14, a block diagram of the major hardware components used in a laser transmitter for one of the laser controllers is illustrated, and is generally designated by the reference numeral 400. Laser transmitter 400 includes a processing circuit 410, which will have associated random access memory (RAM) at 412, associated read only memory (ROM) at 414, and at least one input/output circuit at 416. These devices 412, 414, and 416 communicate with the processing circuit 410 by use of a bus 418, which typically is referred to as an address bus or a data bus, and can also contain other types of signals, such as interrupts and perhaps other types of timing signals.

The input/output circuit 416 will sometimes also be referred to herein as an I/O circuit. This I/O circuit 416 is a primary interface between the real world devices and the processing circuit 410. It is in communication with various communications devices and also various types of motor drive circuits and sensor circuits.

The input/output circuit 416 is in communication with a communications port A, which is generally designated by the reference numeral 420. Communications port 420 includes a transmitter circuit 422 and receiver circuit 424. Communications port 420 is provided to exchange data information with the remote controller 600—see FIG. 15. The communication link between remote controller 600 and communications port 420 is designated by the reference numeral 426. In a preferred mode of this system, the communication link 426 will be wireless, although certainly a cable could be connected between the communications port 420 and the remote controller 600, if desired.

A second communications port, referred to as port B, is generally designated by the reference numeral 430 on FIG. 14. This port 430 comprises a data interface with an input circuit at 432 and an output circuit at 434. Communications port 430 transfers data to and from a null-position photosensor, generally designated by the reference numeral 500, using a communication path 436. While it would be possible for communication link 436 to be wireless, there is no particular need for that to be so. The null-position photosensor 500 will typically be mounted directly on the laser controller 130, 140, as will be the laser transmitter 400. Therefore, a direct "wired" link will be typical.

Laser transmitter 400 also includes a leveling motor drive circuit, generally designated by the reference numeral 440. This drive circuit provides the voltage and current for a leveling motor 442. In addition, it receives signals from a level sensor 444, and these input signals will determine what types of commands will be sent to the motor 442 from the drive circuit 440. If desired, this can be a self-contained system that may not need to communicate with the processing circuit 410. However, the laser transmitter 400 will typically desire knowledge of whether or not the laser controller has actually finished its leveling function before the laser transmitter begins to function in its normal mode of operation. In addition, the processing circuit 410 may well desire to control the leveling motor drive circuit 440, essentially to keep it de-energized at times when it is not critical for the laser controller to actually be attempting to level itself with respect to gravity.

Laser transmitter 400 also includes an angle encoder 450, in a preferred embodiment. Angle encoder 450 will provide input signals to the processing circuit 410, so that it knows exactly where the laser transmitter is being pointed with respect to the azimuth direction. This could be a wholly manual operation, if desired to reduce system cost by eliminating the encoder. However, for a fully automated system, the angle encoder 450 will be necessary.

Laser transmitter 400 preferably will also include an azimuth motor drive, generally designated by the reference numeral 460. Motor drive 460 will provide the proper current and voltage to drive the azimuth motor 462, which is the motive force to aim the laser transmitter. This again could be part of a self-contained system, working with the angle encoder 450; however, on FIG. 14, it is illustrated as being controlled by the processing circuit 410.

Laser transmitter 400 also includes a laser light source driver circuit 470, which provides the current and voltage to drive a laser light source 472. This typically will be a laser diode, although, if desired, it could be an other type of laser light beam emitter. As described above, the laser light source will typically be emitting visible light, although a non-visible light source could be desirable for certain applications, and a laser light source emitting infrared light could be used in that situation. The laser source driver 470 is controlled by processing circuit 410 in the configuration illustrated on FIG. 14.

The laser controller 130, 140 will typically use a "fan beam" laser transmitter for use in the overall point layout computer system. However, it will be understood that other types of laser light sources could be used, including a rotating laser beam, if desired. However, there must be some minimum amount of divergence to create a laser light "plane" so that the laser light will at least intersect the floor surface of a jobsite, and preferably also intersect a ceiling surface for enclosed spaces on jobsites. The point layout system will have many uses, even if the laser light source only is pointing at a floor surface, but point layout system expands its usefulness if the divergence angle of the laser plane is designed to intersect not only the floor, but also the ceiling of the enclosed space. In this description, it will be assumed that the laser light source is a fan beam laser, and so a continuous plane of laser light is being emitted by each laser transmitter at both laser controllers 130 and 140.

Figure 15:
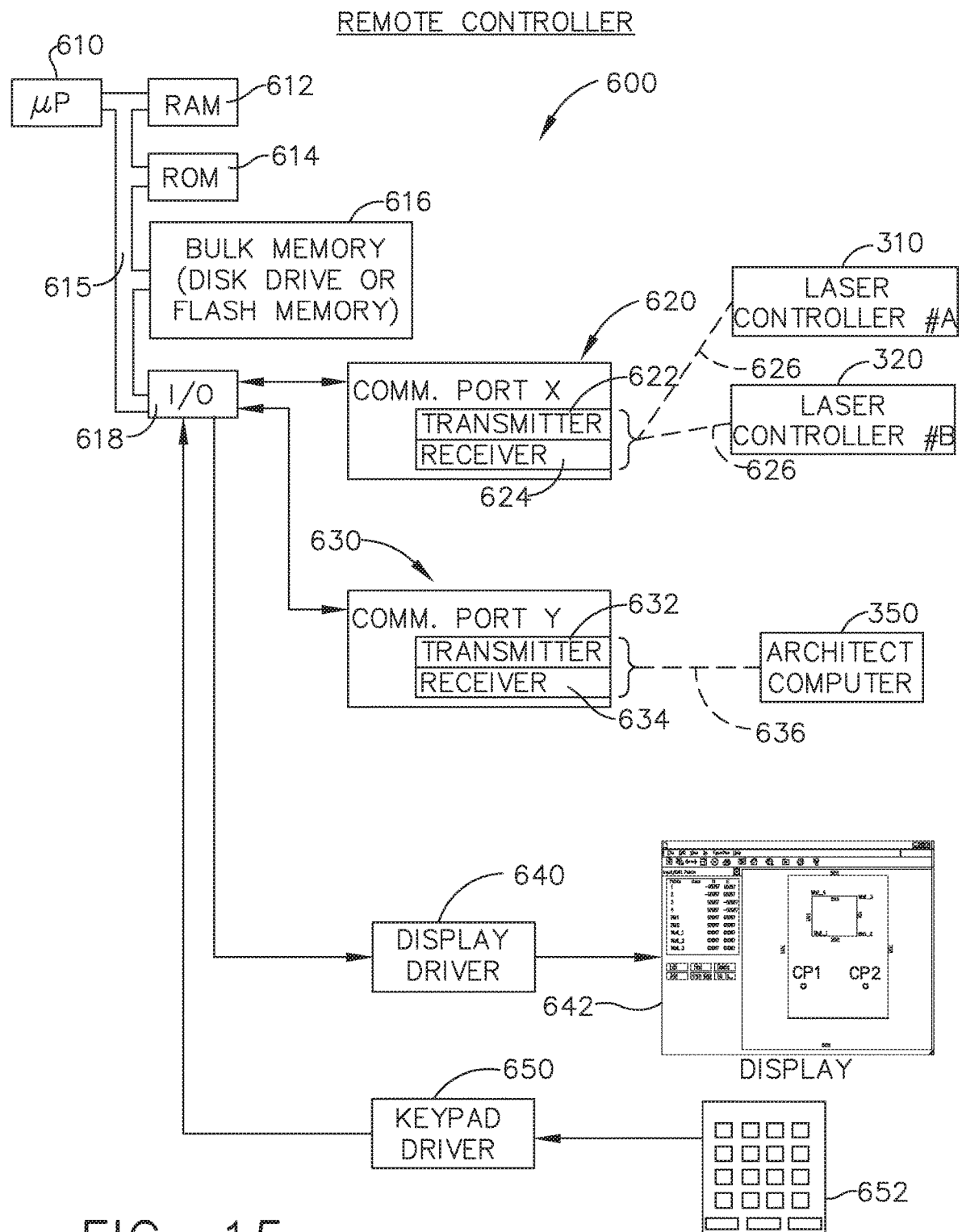
FIG. 15 is a block diagram of the major components of a remote controller that is used in the technology disclosed herein, as constructed according to the principles of the technology disclosed herein.

Referring now to FIG. 15, a block diagram is provided for a remote controller, which is generally designated by the reference numeral 600. Remote controller 600 includes a processing circuit 610, with associated RAM 612, ROM 614, some type of bulk memory or external memory 616, and an input/output circuit 618. These circuits are all in communication with the processing circuit 610 via a bus 615, which normally would carry data signals and address signals, and other types of microprocessor signals, such as interrupts.

On FIG. 15, the communications between the remote controller 600 and multiple laser controllers 310 and 320 (the same as laser controllers 130, 140 on FIG. 17) typically is wireless, such as using a WiFi signal format. The remote controller can be a standard tablet computer or a smart phone, for example, with a custom APP installed to work in the Point Layout System. A standard tablet computer typically includes a WiFi transmitter/receiver circuit 620, so the WiFi format should work well if each of the laser controllers includes a compatible wireless transmitter/receiver circuit.

The bulk memory 616 could be a disk drive, or perhaps some type of flash memory. If in the form of flash memory, it could be an external memory device (such as a "portable memory device") that can plug into the remote controller, via a USB port, for example. In that situation, there would be a USB interface between the bulk memory device 616 and the bus 615.

The I/O circuit 618 will be in communication with a first communications port 620, which is designated as communications port "X" on FIG. 15. Communications port 620 includes a transmitter circuit 622, and a receiver circuit 624. Communications port 620 is designed to communicate with the laser controllers 310 and 320, typically using a wireless signal via a wireless pathway 626 (as noted on FIG. 15). As described in greater detail below, the laser controllers 310 and 320 will communicate azimuth angular information with the remote controller, and that information arrives via the wireless path 626 to and from communications port 620.

A second communications port 630 is included in remote controller 600, and this is designated as communications port "Y" on FIG. 15. Communications port 630 includes a transmitter circuit 632 and receiver circuit 634. This communications port 630 is provided to exchange information with an architect computer 350, via a communication link 636. On FIG. 15, communication link 636 is depicted as a wireless link, although it certainly could be constructed by use of an electrical cable or an optical cable, if desired.

If wireless signals are not desired (or are not operating properly for some reason), then it is also possible to attach a USB cable between the remote controller 600 and each of the laser controllers 310 and 320, as needed, to communicate messages between those controllers.

Assuming a virtual jobsite illustration is available on an architect computer 350, then that virtual jobsite illustration can be downloaded to the remote controller 600 using an e-mail message, for example. In other words, if the virtual jobsite illustration is stored in an office on a standard personal computer that never leaves the office, then the virtual jobsite illustration can be sent as a file to an e-mail address over the Internet. The tablet computer that acts as the remote controller 600 could be the home of that e-mail address (or could remotely access that e-mail address, if desired), and thus upload that file into the memory circuit (into RAM 612 or the Flash memory 616) of the remote controller 600. The format of that virtual jobsite illustration is up to the architect, but typically it would be a two-dimensional or three-dimensional CAD file (and often referred to as a "CAD model").

The block diagram of FIG. 15 includes some typical hardware for microprocessor-driven devices, such as tablet computers, as noted above. For example, the visual display 642 of a tablet computer or a smart phone would typically have a display driver circuit 640, and the keypad 652 would typically have a keypad driver circuit 650. It should be noted that the keypad 652 can be a virtual keypad, as would be typical for a touchscreen display (as found on many tablet computers and smart phones).

It should be noted that, although the block diagram for the remote controller 600 as depicted on FIG. 15 includes two separate communication ports "X" and "Y" (at communications circuits 620 and 630), it is clear that a single communications circuit could instead be used, in which the software of the remote controller's APP would control how and when that single communications circuit would send and receive messages to and from one of the laser controllers 310 or 320, or would send and receive messages to and from the architect computer 350.

Communications port 630 will exchange floor layout data with the architect computer 350; more specifically, it can receive a virtual jobsite illustration and store it in the bulk memory circuit 616. In addition, if the remote controller 600 receives information about a new or "unknown" point of interest in the physical jobsite floor plan, then that information can not only be saved in the bulk memory circuit 616, but could be also communicated back to the architect computer 350, via the communications port 630 to be placed in the original virtual jobsite illustration. Or, a revised virtual jobsite illustration (which includes the new point of interest) can be saved as a file in bulk memory circuit 616, and that entire file could be transferred to the architect computer 350.

It will be understood that the architect computer 350 could comprise a "fixed" unit that essentially remains in the architect's office, and passes data to the remote controller 600 while the remote controller is physically at the office, or perhaps they remotely communicate with one another via a wide area network, such as the Internet. Alternatively, the architect computer 350 could comprise a "portable" unit that is transported to the jobsite, and communicates with portable remote controller 600 while on site. Finally, as portable computers become even smaller in physical size, it is more likely that the portable remote controller 600 and the architect computer will eventually become merged into a single device. (On the other hand, the construction worker who is performing the actual point layout work will likely need his own tablet computer at all times.)

A display driver circuit 640 is in communication with the I/O circuit 618. Display driver circuit 640 provides the correct interface and data signals for a display 642 that is part of remote controller 600. If remote controller 600 is a laptop computer, for example, then this would be the standard display seen in most laptop computers. Or, perhaps the remote controller 600 is a calculator-sized computing device, such as a PDA (Personal Digital Assistant), in which case the display would be a much smaller physical device. Display 642 could be a touchscreen display, if desired.

One example of a type of remote controller that could work in this system (with some modification) is the portable "layout manager," which is an existing hand held computer, Model Number LM80, sold by Trimble, Inc. It should be noted that one cannot simply take the LM80 and immediately use it as a remote controller in the present system; the software must be modified to perform the necessary calculations. In addition, the input/output circuits typically must be modified to be able to communicate commands and data both to and from the laser controllers 310 and 320.

A keypad driver circuit 650 is in communication with I/O circuit 618. Keypad driver circuit 650 controls the signals that interface to a user input sensing device 652, such as a keypad, as depicted on FIG. 15. Again, if the display 642 is of a touchscreen type, then there may not be a separate keypad on remote controller 600, because most of the command or data input functions will be available by touching the display itself. There may be some type of power on/off switch, but that would not necessarily be considered a true keypad (and typically would not be used for entering data).

It should be noted that the remote controller 600 can be constructed of almost any kind of computer, although to best accomplish the functions described herein, the remote controller will likely be a portable computer (such as a tablet computer or a smart phone) that is small enough to be easily moved about the jobsite. However, a larger computer could be used, if desired, such as a standard-sized laptop computer. Many portable computers are provided with a touchscreen display, and that type of hardware works well in the Tap 'N Go system.

Figure 16:
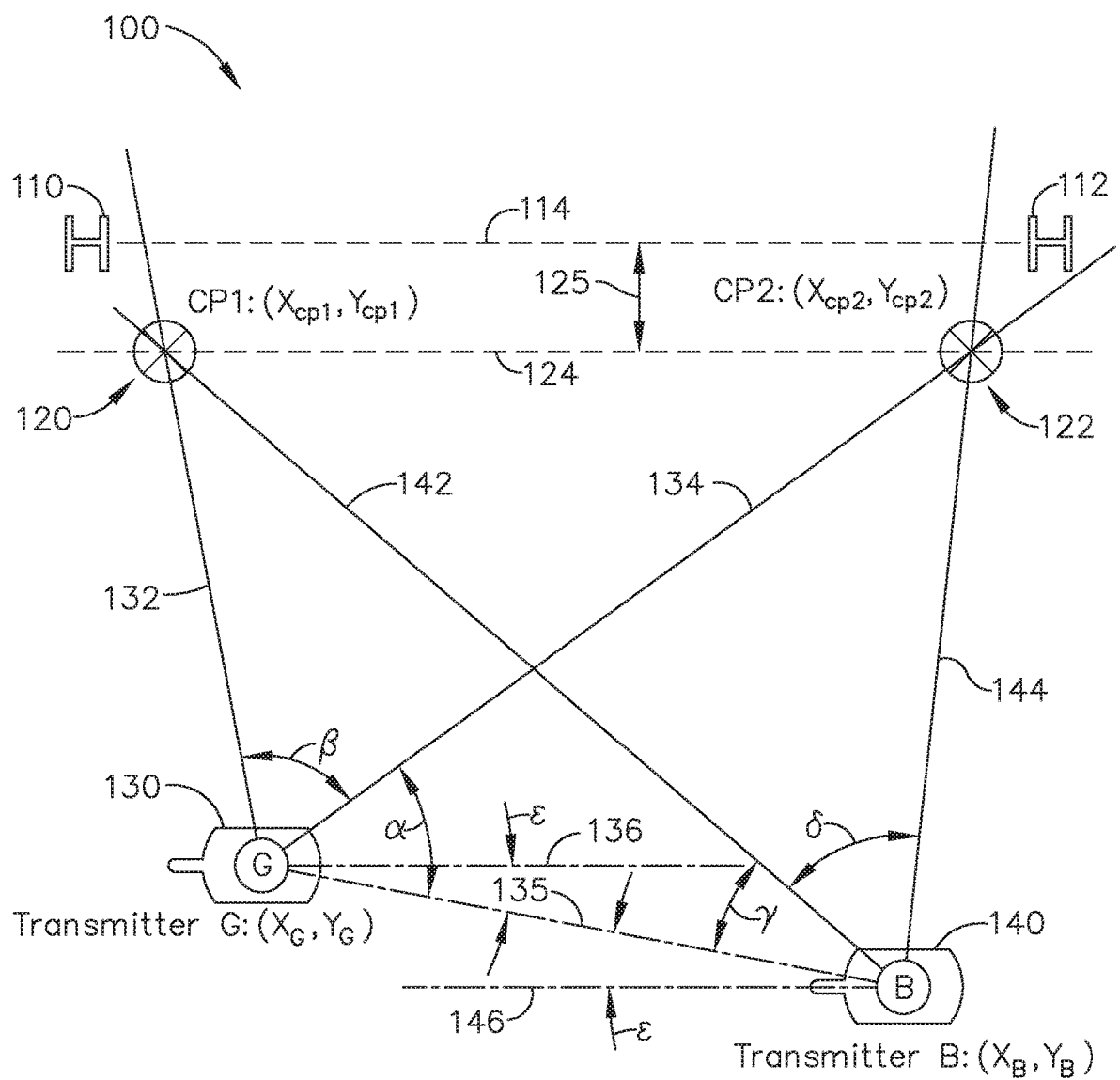
FIG. 16 is a diagrammatic view of a jobsite floor showing positions of I-beam uprights with a centerline, a parallel chalk line with control points, and two laser controllers of the type that have rotatable laser transmitters that produce vertical fan beams, in which the laser controllers are involved in an initial setup routine.

Referring now to FIG. 16, a portion of a jobsite floor is depicted in an elevational view, which includes two vertical I-beams at 110 and 112, which are typically referred to as uprights. As is done with many jobsite floor layout situations, a chalk line is often snapped between the centers of these two I-beams 110 and 112, creating a snapped chalk line 114. Since it is difficult to work directly through a line that travels through uprights, the workers on the jobsite will typically offset a second chalk line by a certain distance, in which that offset chalk line is parallel to the original centerline between the I-beams. Thus a second chalk line 124 is snapped parallel to the initial chalk line 114. All of this is shown in this view of the jobsite floor that is generally depicted by the reference numeral 100.

Two control points CP1 and CP2 are selected along the offset chalk line 124. The locations of these control points are designated by the reference numerals 120 and 122 on FIG. 16. These control points may be known on this virtual jobsite illustration, or if they need to be created from the jobsite's drawings, that can be done by proper surveying techniques. In any event, control points 120 and 122 will become known points on the actual jobsite floor, and also on the virtual jobsite illustration that is in the database of the architect computer (not shown), in which that virtual jobsite illustration will also be used for the remote controller 600 that will be available on the actual jobsite for use by the users working with the laser controllers.

The offset distance is designated by the reference numeral 125 on FIG. 16, and that can either be predetermined if the control points 120 and 122 are themselves predetermined or, if desired, this offset distance can be selected by the jobsite workers. As noted above, the coordinates on the jobsite floor must become known for these two control points. A typical distance for the offset amount would be two feet (which would be the dimension noted at reference numeral 125).

It is now time to begin setting up the laser controllers that include laser transmitters. In this example of FIG. 16, there will be two different laser controllers 130 and 140. It should be noted that each of these laser controllers can be identical in all respects, although it can be advantageous to use a different color for the beacon signal (or beacon lamp) that will typically be available on each of the laser controllers. For example, on FIG. 16, the laser controller 130 may have a green color lamp for its beacon, hence the letter "G" is used on the drawing. The laser controller 140 may have a blue color beacon lamp, hence the use of the "B" on the drawing of FIG. 16.

As can be seen by viewing FIG. 16, the laser transmitters can "aim" at each of the control points 120 and 122, and the aiming lines from the laser transmitter of the first laser controller 130 are designated by the reference numerals 132 and 134, aiming at the respective control points 120 and 122. Similarly, the aiming lines from the laser transmitter for the second laser controller 140 are designated by the reference numerals 142 and 144, aiming at the control points 120 and 122, respectively. At this time, and knowing information which includes the azimuth directions for all these various aiming lines for each of the laser controllers, these two laser controllers now become set up with the control points, using an automatic axis alignment procedure, as discussed in other patent documents that are incorporated herein by reference. The axis of alignment between the two laser controllers is designated by the reference numeral 135 on FIG. 16. Now that the laser controllers 130 and 140 are aligned with one another, the azimuth angles of the aiming lines can be measured, thereby giving the actual angles $\alpha$, $\beta$, $\delta$, and $\gamma$. This information now allows the coordinates of these two laser controllers 130 and 140 to now be calculated with respect to the virtual jobsite illustration.

Equations for calculating the positions of the laser controllers in terms of the "jobsite coordinates" in the virtual jobsite illustration drawings are provided in other patent documents, such as patent application Ser. No. 15/351,170, filed on Nov. 14, 2016 (not yet published). The notations on FIG. 16 for the coordinates of CP1, CP2, laser controller 130, and laser controller 140 {i.e., the notations $(X_{cp1}, Y_{cp1})$, $(X_{cp2}, Y_{cp2})$, $(X_G, Y_G)$, and $(X_B, Y_B)$} would typically be available to the user in numeric units of the virtual jobsite illustration coordinates, by viewing the display of remote controller 600.

Referring now to FIG. 17, a pair of laser controllers at reference numerals 130 and 140 are placed on a jobsite surface at 103, and are used in a 2-dimensional point layout system. The system of FIG. 17 is an advanced point layout system, and there are two patent documents which disclose certain embodiments of this system. The first document is U.S. Pat. No. 8,087,176, and the second document is U.S. Pat. No. 8,943,701; both patent properties are commonly-assigned to Trimble Navigation Limited (now known as Trimble, Inc.).

In this system of FIG. 17, both laser controllers have laser vertical fan beams that are emitted by turret heads that have a laser fan beam emitter. These two turret head fan beam emitters are at 131 and 141, respectively, for the laser controllers 130 and 140. The fan beam emitted by the turret head 131 has an upper edge line at 133, and a lower edge line at 135. As can be seen in FIG. 17, once the lower edge line 135 reaches the floor surface, it produces a visible laser light line at 137, which continues all the way across the floor. In essence, there is a laser light curtain (or plane of laser light) between the edge lines 135 and 133, and that laser light curtain is essentially a vertical laser plane, and is generally designated by the reference numeral 139.

In a similar fashion, the second laser controller emits a laser fan beam from the turret head 141, which has a top edge line 143 and a bottom edge line 145, and which produces a curtain or plane of laser light, commonly designated by reference numeral 149. Once the lower edge line 145 strikes the floor surface 103, it produces a visible laser light line 147 that runs all the way across the floor.

On FIG. 17, the two laser light lines 137 and 147 intersect at a point 105. Assuming this was an actual jobsite, such as a construction site where a building is being erected, for example, the point 105 might be a benchmark, or it could be some other type of point of interest. In any event, it is desired for both laser controllers to have their fan beams aimed at the point of interest 105, so that their light lines 137 and 147 actually intersect at that point. When that occurs, a vertical laser light line will exist where the two planes of laser light 139 and 149 intersect, just above the point 105. That vertical laser line is designated by the reference numeral 107 and truly is a plumb line extending from the floor surface 103 up to the ceiling, or higher if there is no ceiling. In essence, the laser plumb line 107 will exist from the lower point 105 all the way to an upper point where the two top edge lines 133 and 143 intersect each other's laser planes. (More precisely, the top portion of the vertical plumb line 107 of laser light will extend all the way to the lower of the two top edge lines 133 and 143, where the two laser planes 139 and 149 intersect.)

Figure 18:
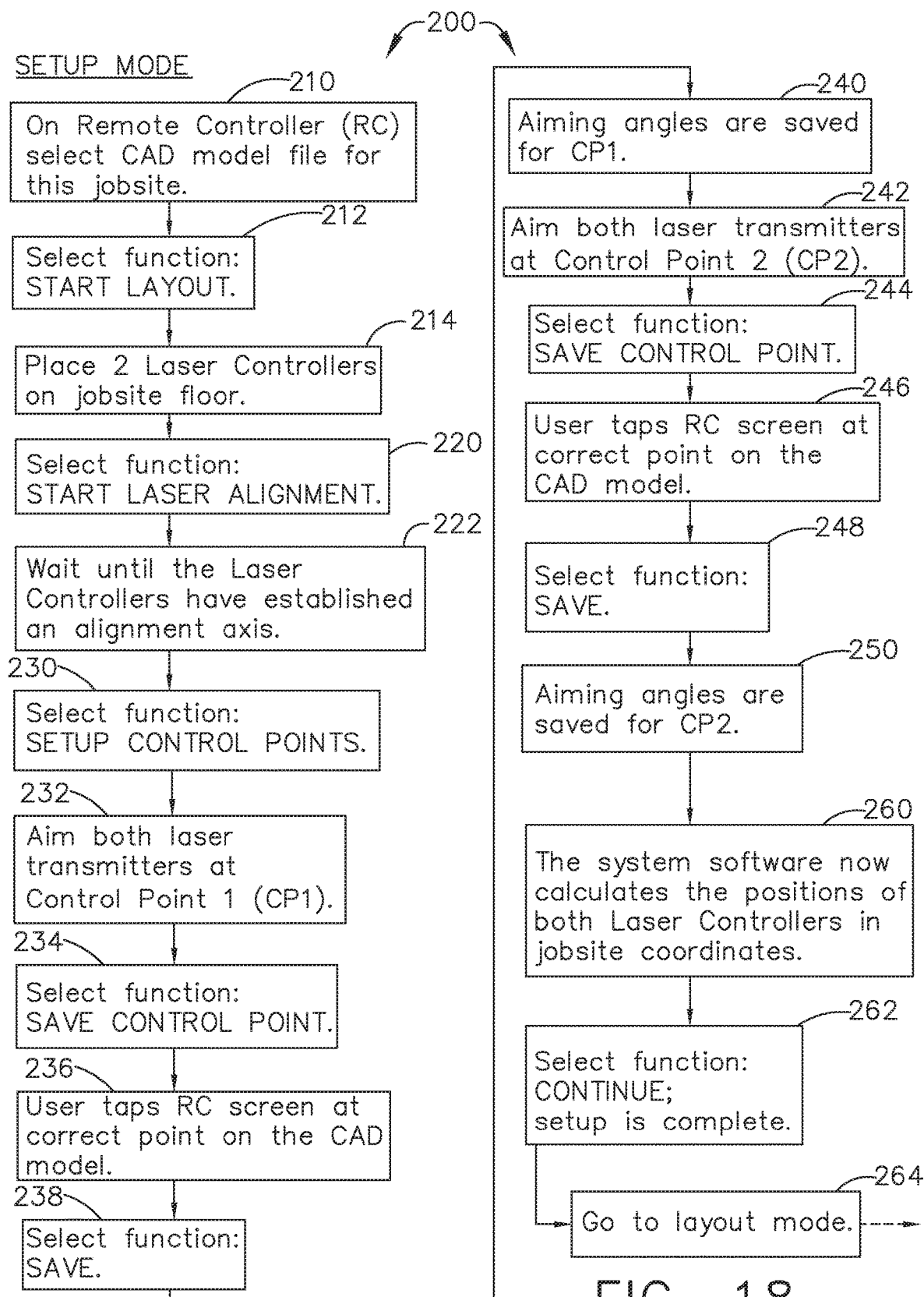
FIG. 18 is a flow chart of some of the important steps performed in a setup mode of operation, using the software concepts described according to the principles of the technology disclosed herein.

Referring now to FIG. 18, a flow chart is provided showing the setup mode for this system. The overall flow chart is designated by the reference numeral 200, and begins at a step 210 in which a particular CAD model file is selected by the user on the remote controller. The user then selects a function called "START LAYOUT," at a step 212. The user now places two laser controllers on this jobsite floor, at a step 214 on this flow chart.

The user now selects a function called "START LASER ALIGNMENT," at a step 220. Using laser controllers that are available from Trimble Inc. of Sunnyvale, Calif. (now known as Trimble, Inc.), the laser controllers will automatically establish an alignment axis between themselves, and this occurs at a step 222 on this flow chart.

The user now selects a function called "SETUP CONTROL POINTS," at a step 230. The user now aims both laser transmitters at control point #1, in a step 232. After that has occurred, the user selects a function called "SAVE CONTROL POINT," at a step 234. The user now taps the remote controller screen at the appropriate point on the CAD model that is depicted on the touchscreen display of that tablet computer 600, at a step 236 of this flow chart. The user now selects a function called "SAVE," at a step 238. This causes the aiming angles of both of the laser controllers to be saved in memory for the first control point, at a step 240.

The user now aims both laser transmitters at the second control point, at a step 242 of this flow chart. The user now selects a function on the tablet computer (the remote controller 600) called 'SAVE CONTROL POINT," at a step 244. The user now taps the touchscreen display of the remote controller 600 at the appropriate correct point for this CAD model that is displayed on that tablet computer's screen, at a step 246 of this flow chart. The user now selects a function called "SAVE," at a step 248. The aiming angles of both laser transmitters are now automatically saved for the second control point, at a step 250.

Since the two control points are at known positions on the jobsite floor, the system software can now determine exactly where the two laser controllers 130 and 140 are located. A step 260 now calculates the positions of both laser controllers in terms of the jobsite coordinates. These laser controllers can now be used for laying out points of interest all over the jobsite floor.

The user now selects a function called "CONTINUE," at a step 262. The setup of these two laser controllers 130 and 140 is now complete. The next step 264 will automatically take the remote controller operating software to the layout mode.

Figure 19:
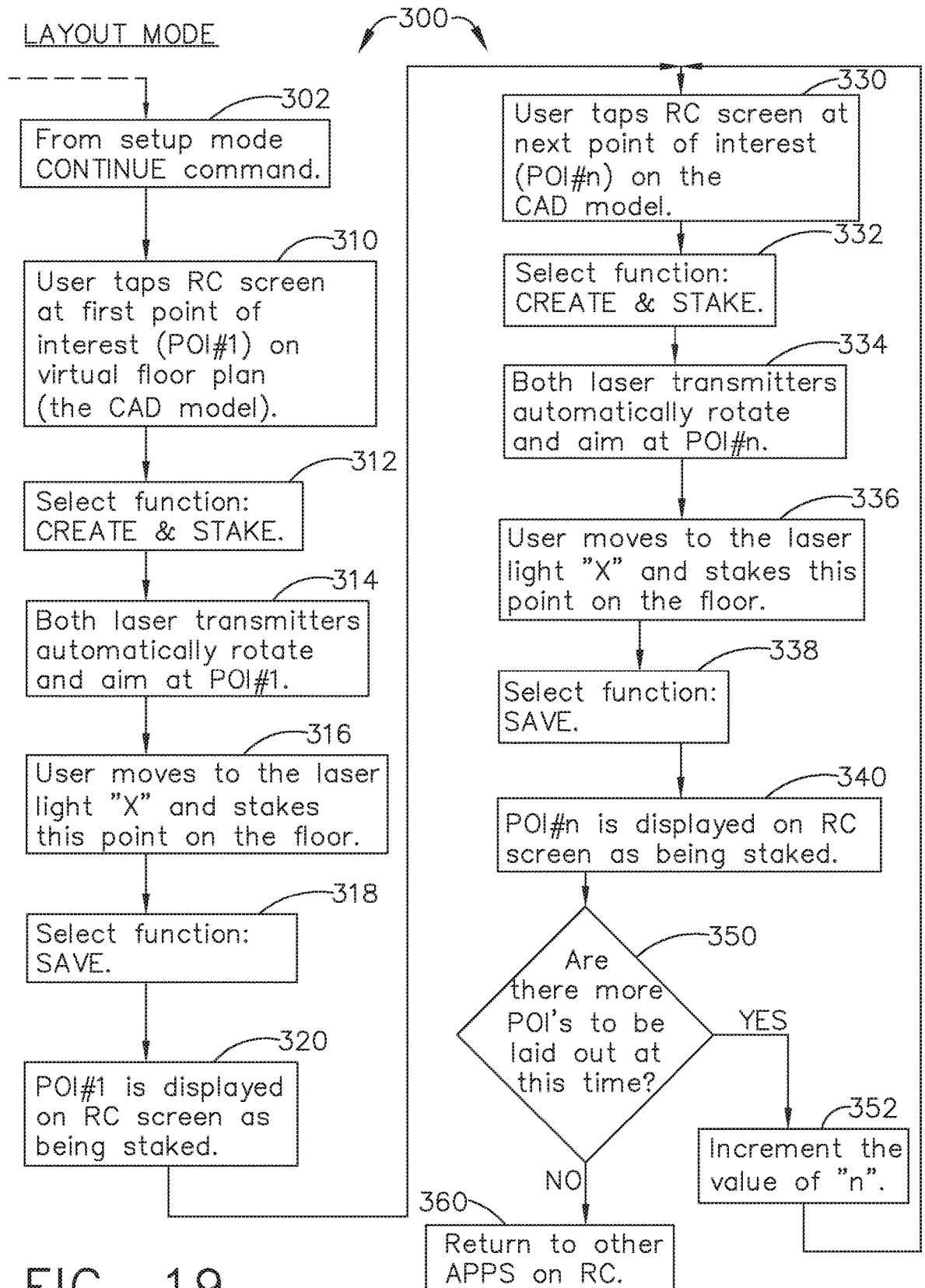
FIG. 19 is a flow chart of some of the important steps performed in a layout mode of operation, using the software concepts described according to the principles of the technology disclosed herein.

Referring now to FIG. 19, this is a flow chart for the layout mode of the present technology, and this flow chart is generally designated by the reference numeral 300. The logic flow that arrives at flow chart 300 can automatically come from the setup mode, after the "CONTINUE" function has been executed at the step 262 on FIG. 18.

Beginning at step 302, this logic sequence continues from that CONTINUE command, and proceeds into the layout mode of operation. A step 310 now occurs in which the user taps the remote controller touchscreen at a first point of interest on the virtual jobsite illustration (i.e., the CAD model). Once that first point has been selected by tapping the screen, the user now selects a function called "CREATE & STAKE," at a step 312. After that function has been selected, both laser transmitters of the two laser controllers 130 and 140 are automatically rotated to aim at the first point of interest (referred to as POI#1) that was selected on the screen, back at step 310. This occurs at a step 314, and is accomplished by the remote controller sending wireless messages to both laser transmitters to command them to rotate to the correct azimuth angle so that they will produce their laser fan beams at the correct angles for the laser light lines to cross right over the first point of interest. The laser light lines will intersect to show a visible "X" that marks the spot so the user can easily find that physical point of interest.

The user now moves to the laser light intersection and stakes this point on the jobsite floor, at a step 316. The user now selects the function "SAVE," at a step 318. The first point of interest is now displayed on the remote controller screen as having been staked, at a step 320.

When the user is ready, he taps the remote controller touchscreen at the next point of interest on the CAD model, at a step 330. The user then selects the "CREATE & STAKE" function at a step 332. This causes both laser transmitters to automatically rotate and aim at the second point of interest, referred to on FIG. 19 as "POI#n." This occurs at a step 334, and operationally it is accomplished by the remote controller 600 sending wireless messages to both of the laser controllers 130 and 140 so that they are commanded to aim their laser fan beams directly at the second point of interest. Their laser light lines will then both cross right at that next point of interest on the physical jobsite floor.

The user now moves to the laser light intersection, which appears as an "X", and then stakes this point on the physical jobsite floor, at a step 336. The user now selects a function called "SAVE," at a step 338. This point of interest is now displayed on the remote controller viewing screen as having been staked, at a step 340.

A decision step 350 is now executed to determine whether or not there are more points of interest to be laid out at this time. If the answer is YES, then a step 352 increments the value of "n", and the logic flow is directed back to the step 330 so the user can select the next point of interest. However, if the answer was NO at decision step 350, then the logic flow will move to a step 360 in which the operating software returns to other apps that are being executed on the remote controller.

Figure 20:
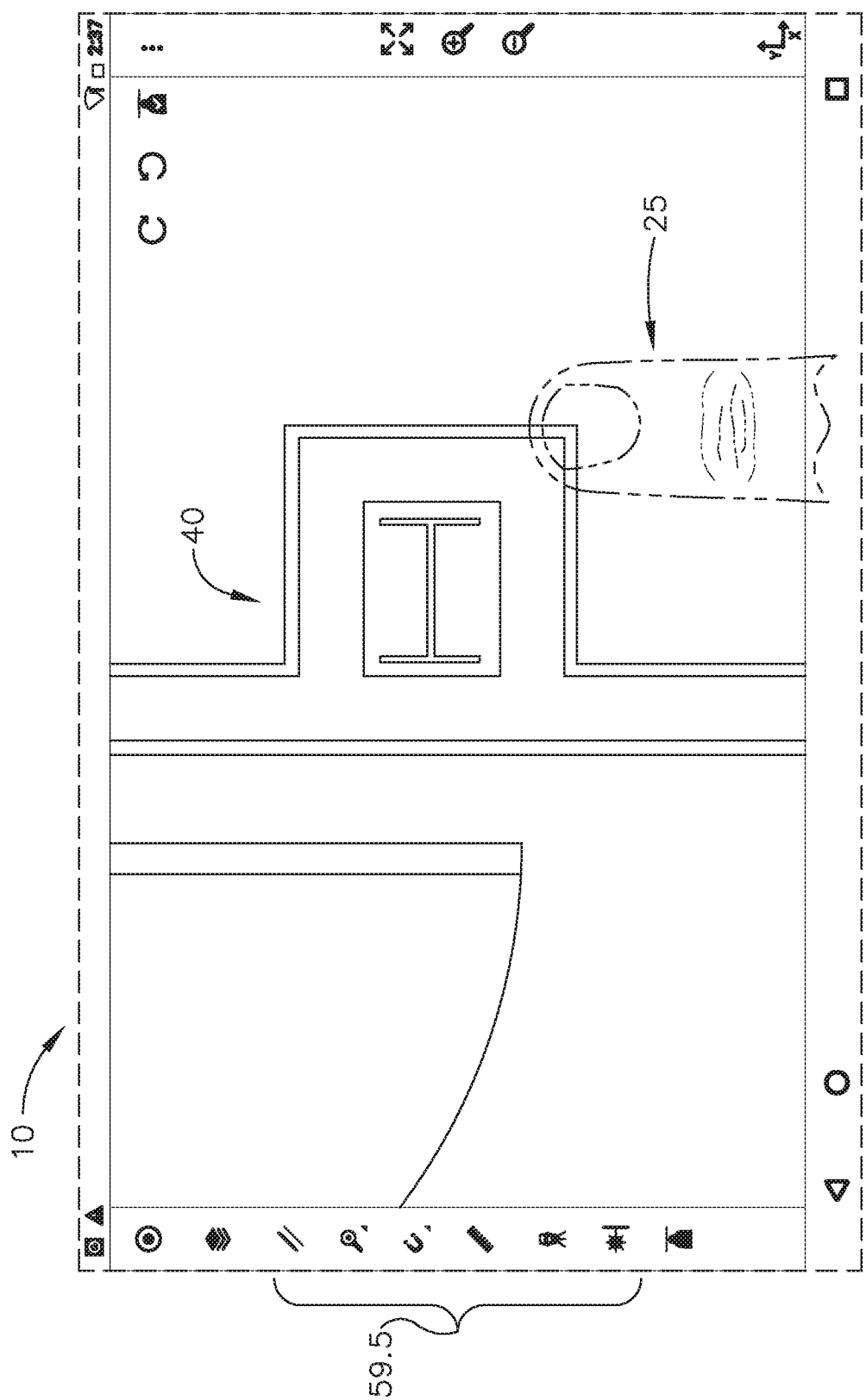
FIG. 20 is a diagrammatic view of a screen shot of the remote controller showing the user's finger tapping the screen, as part of the selection of a point of interest, using the technology disclosed herein.

FIGS. 20-27 are provided to show the ease of use for the operating software of this present technology disclosed herein. This next example also makes apparent the reason that the user-friendly name "Tap 'n Go" has been selected for this particular product. Referring now to FIG. 20, the display screen of the remote controller shows a magnified view that centers on the enclosed I-beam portion of the screen for the architect floor plan of that particular room. This portion is designated by the reference numeral 40. In FIG. 20, the user's finger is illustrated at 25, as tapping the screen at a point that becomes the first point of interest in the above description of the sequence of operations. The screen designation in the sequence of operations is referred to as #59.5, which indicates that it is a screen that would appear before arriving at the screen sequence #60.

Figure 21:
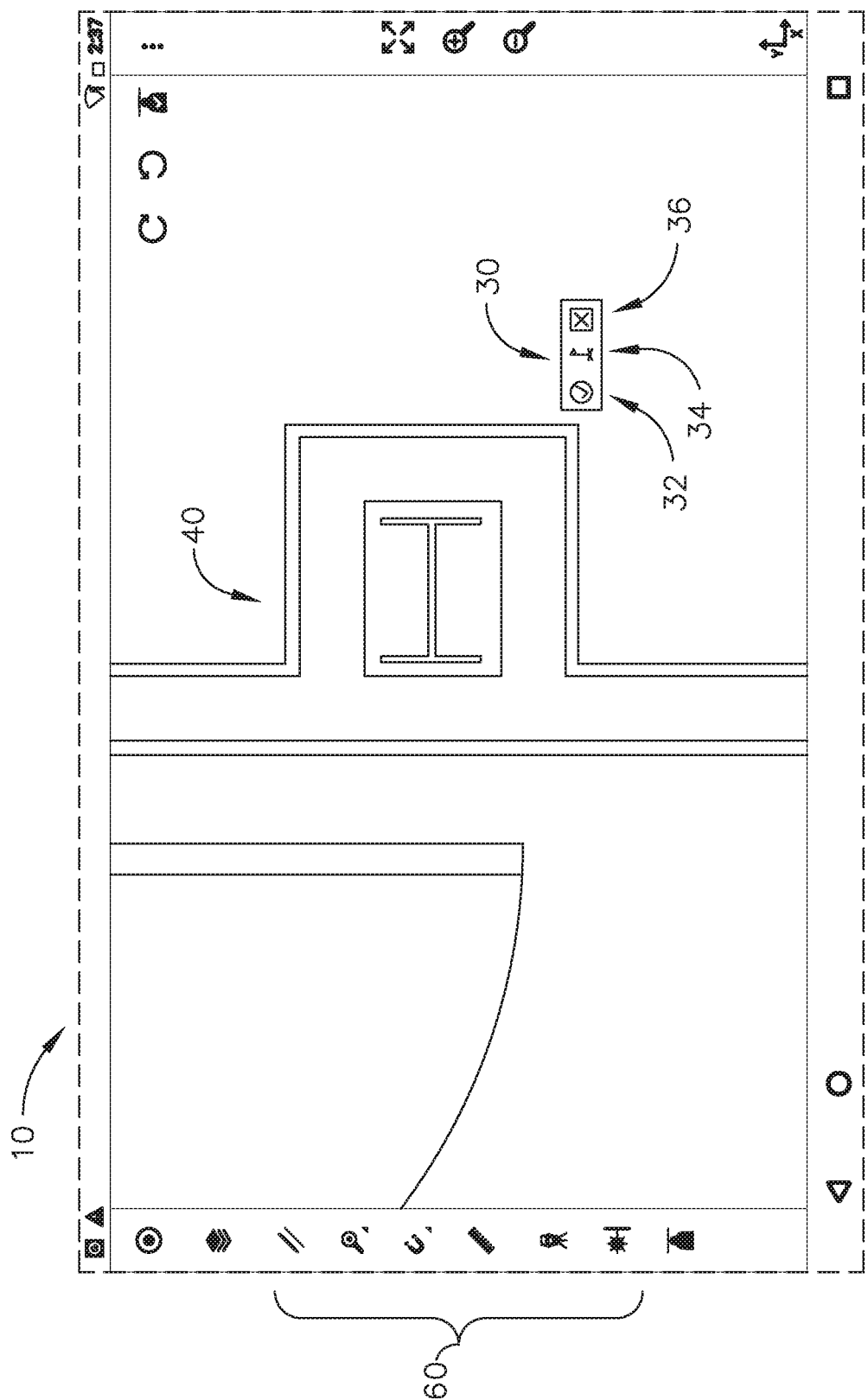
FIG. 21 is a diagrammatic view of a screen shot of the remote controller showing an icon box as an option menu for the first point of interest that was selected in FIG. 20.

FIG. 21 shows the same screen sequence #60 that was also illustrated in FIG. 5. In FIG. 21, the three icons for "CREATE", "CREATE & STAKE", and "CANCEL" are illustrated and designated by the reference numerals 32, 34, and 36, respectively. So if the human user desires to tap CANCEL, for example, then the user would tap the icon that is designated by the reference numeral 36 on FIG. 21.

Figure 22:
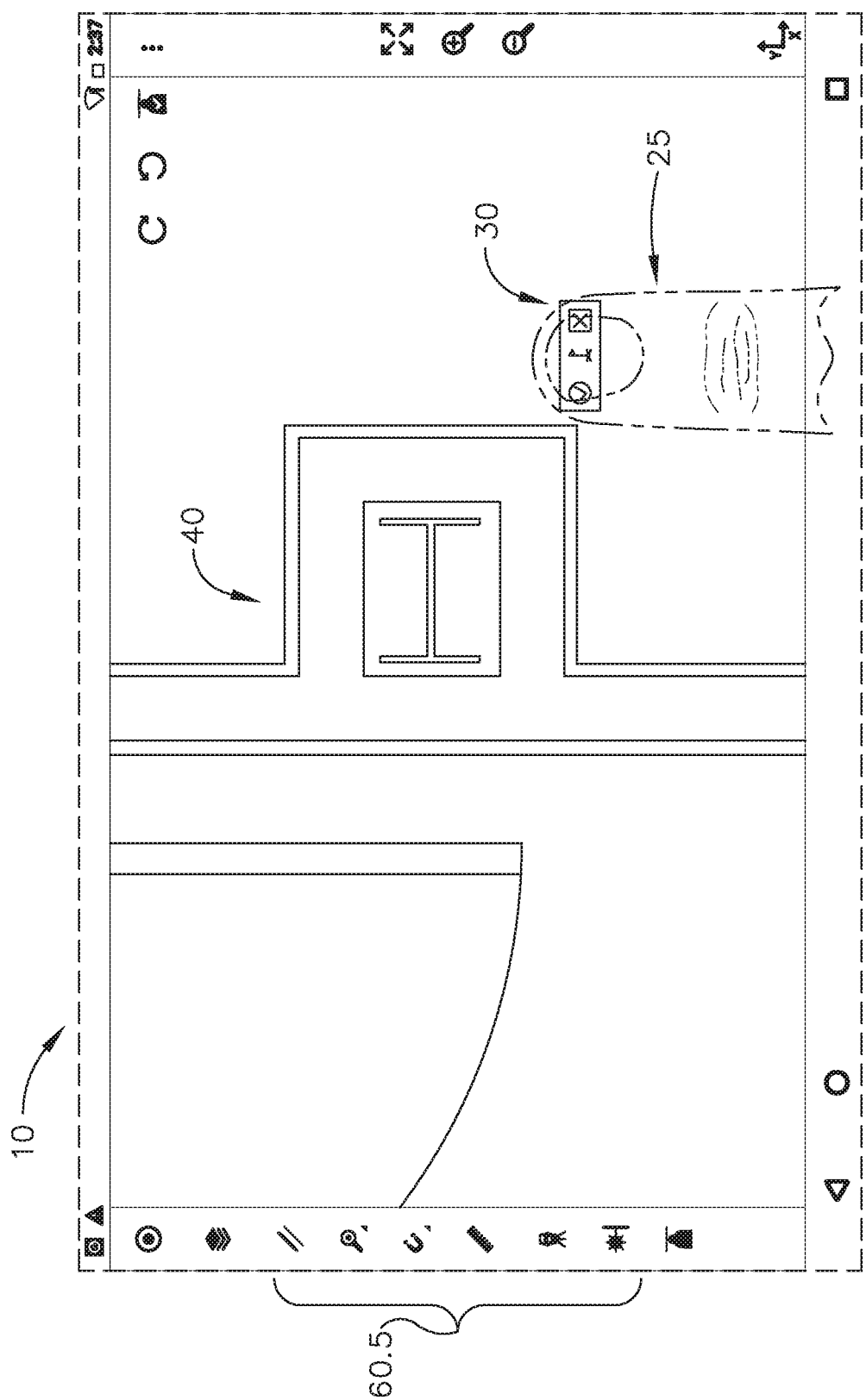
FIG. 22 is a diagrammatic view of a screen shot of the remote controller showing the user selecting the "CREATE & STAKE" choice in the icon box for this first point of interest of FIG. 20.

Referring now to FIG. 22, the user taps the middle icon, which is the "CREATE & STAKE" icon, and that would have the appearance depicted in this view. The drawing sequence designation is #60.5, which shows that this view is in between the drawings having sequence numbers #60 and #61 (which correspond to FIGS. 21 and 23, respectively).

Figure 23:
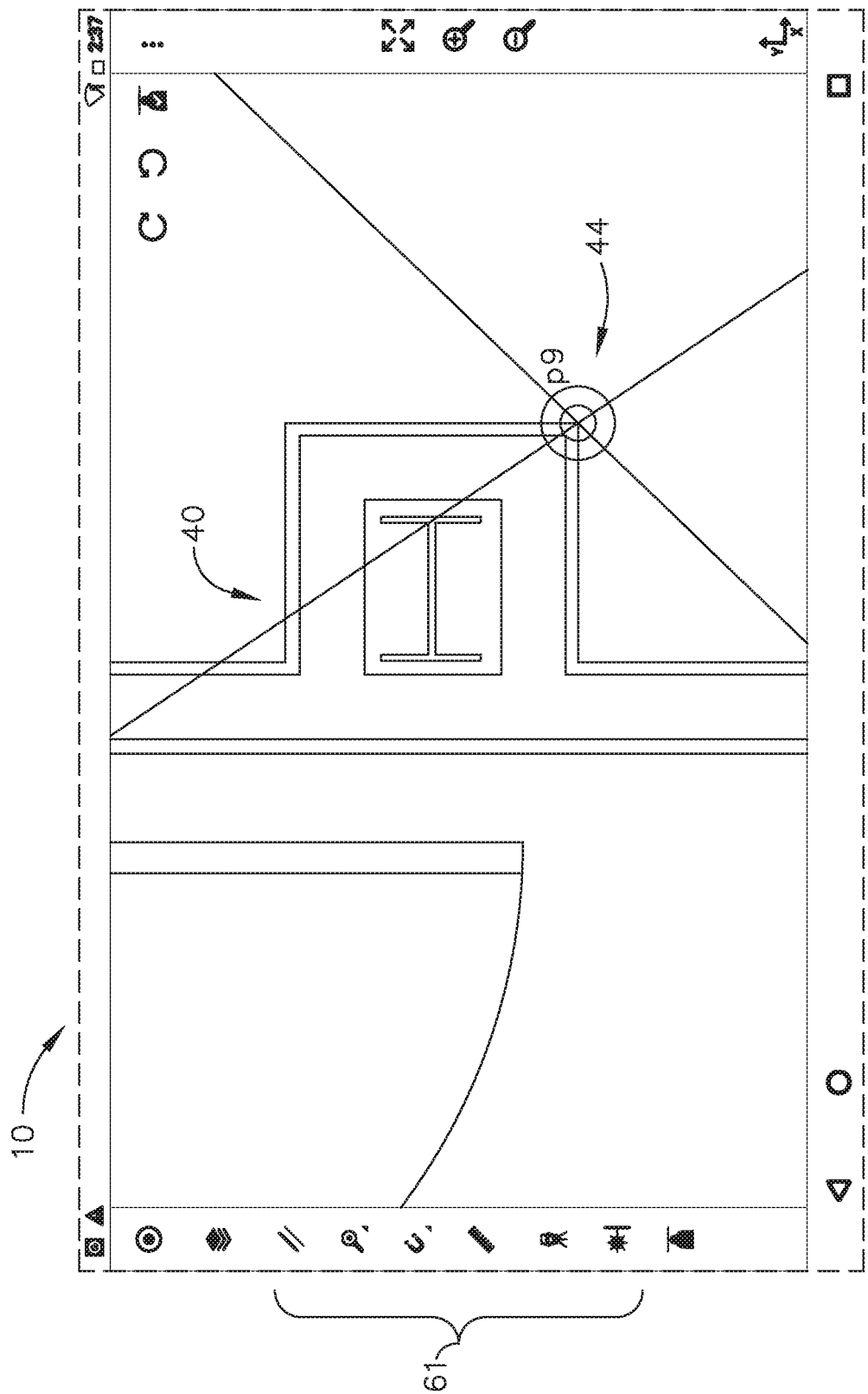
FIG. 23 is a diagrammatic view of a screen shot of the remote controller showing the result of the selection by the user in FIG. 22, and illustrating the status that the first point of interest has now been staked.

After the user taps the CREATE & STAKE icon in FIG. 22, then the view of FIG. 23 appears, which is the drawing sequence #61, and is the same view as FIG. 6. In FIG. 23, the point of interest with the designation "p9" has now been designated as staked, and correspondingly the two concentric circles are now visible on the monitor screen of the remote controller. The user is now ready to select a new point of interest.

Figure 24:
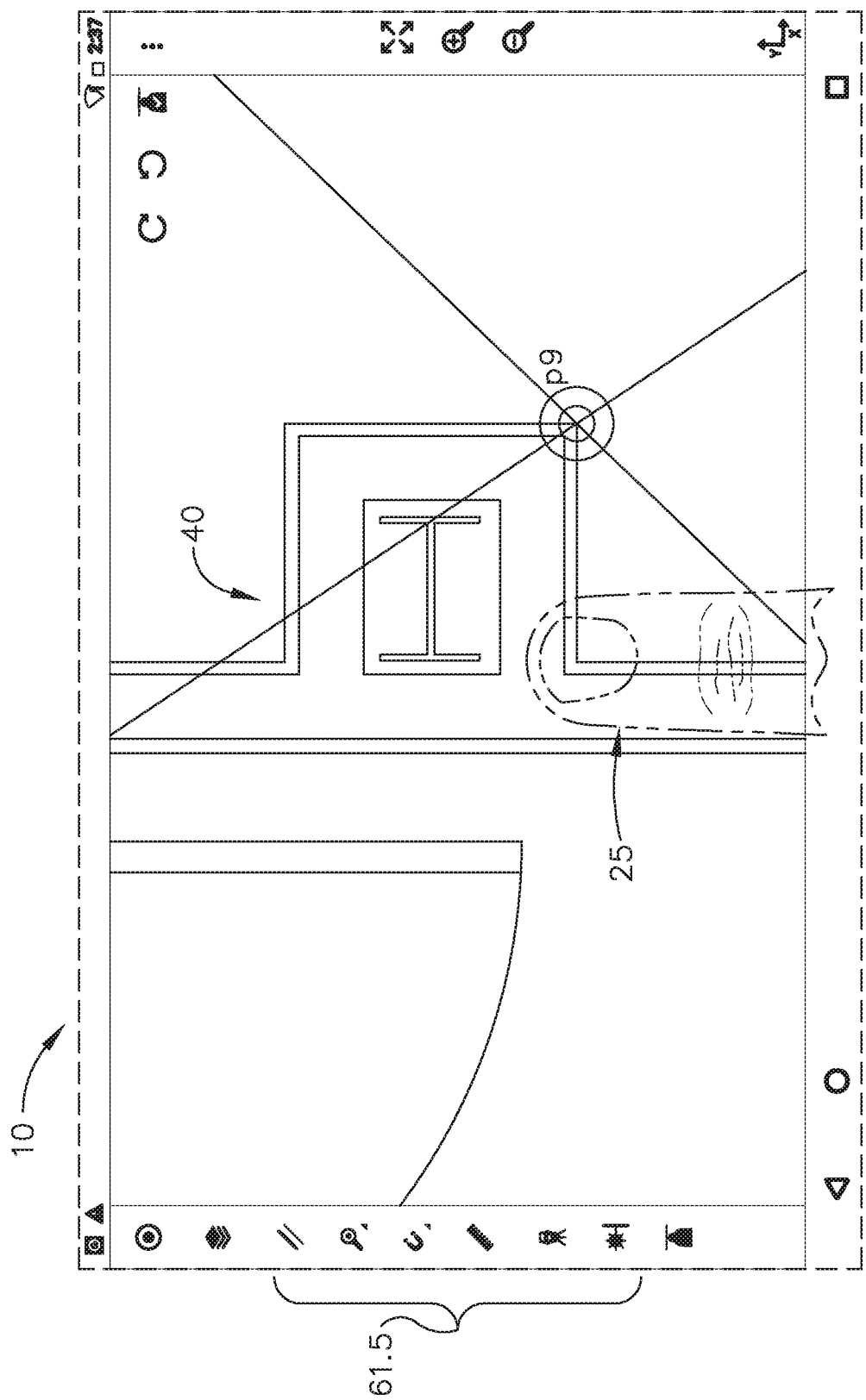
FIG. 24 is a diagrammatic view of a screen shot of the remote controller showing the user's finger selecting a new point of interest by tapping on the touchscreen display of the remote controller.
Figure 25:
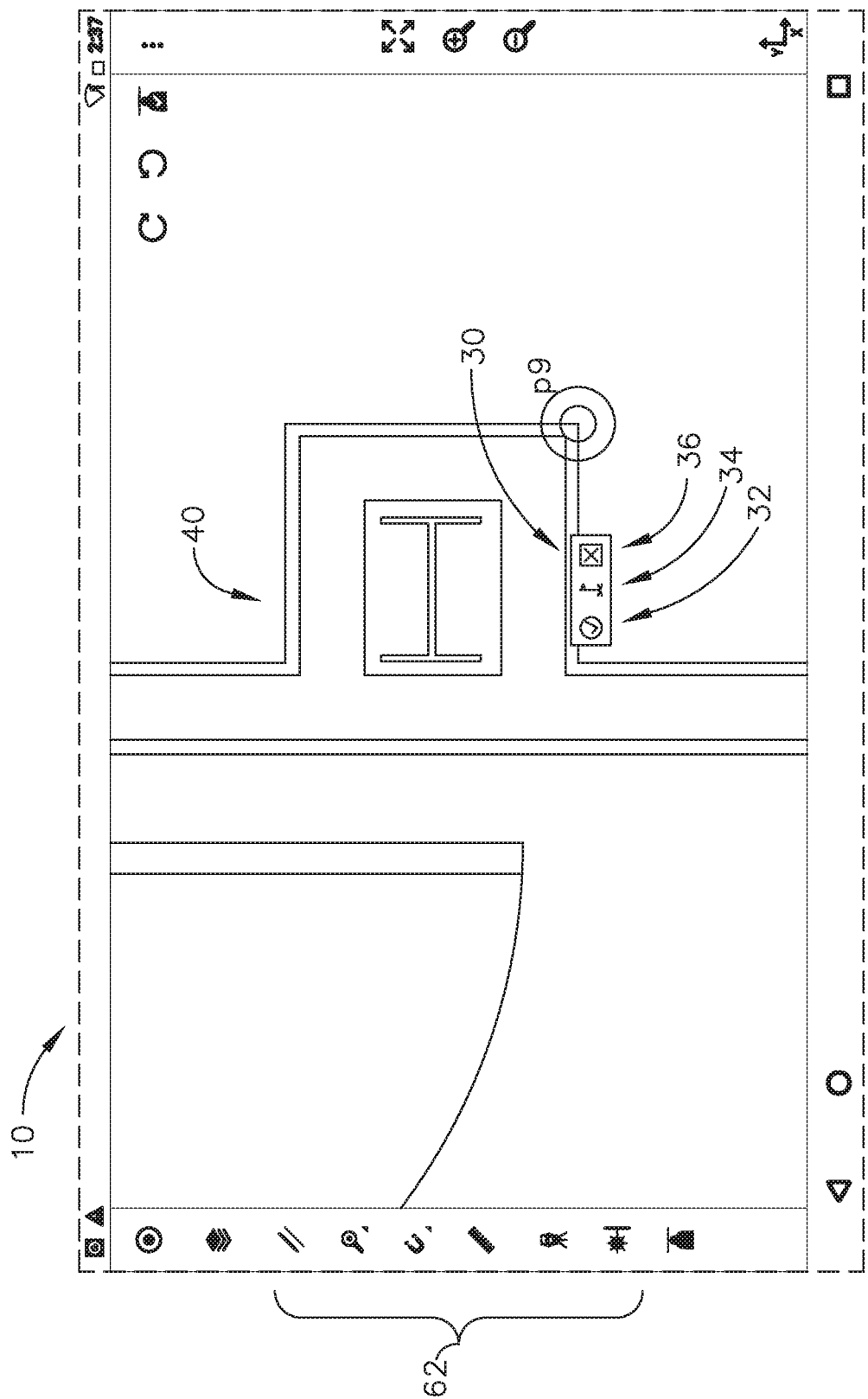
FIG. 25 is a diagrammatic view of a screen shot of the remote controller showing the icon box showing the choices that can now be selected by the user for that second point of interest of FIG. 24.

Referring now to FIG. 24, the user taps the screen at a new location, as seen by the virtual finger 25 on FIG. 24. The sequence designation for this screen is #61.5, which means that this occurs between the screen sequences #61 and #62. After tapping the screen as shown in FIG. 24, the view of FIG. 25 now appears on the tablet computer screen of the remote controller. This shows the small icon box 30 showing the three options available to the user, as designated by the reference numerals 32, 34, and 36, with the same meanings as described above. This is the screen sequence #62, and was also seen in FIG. 7.

Figure 26:
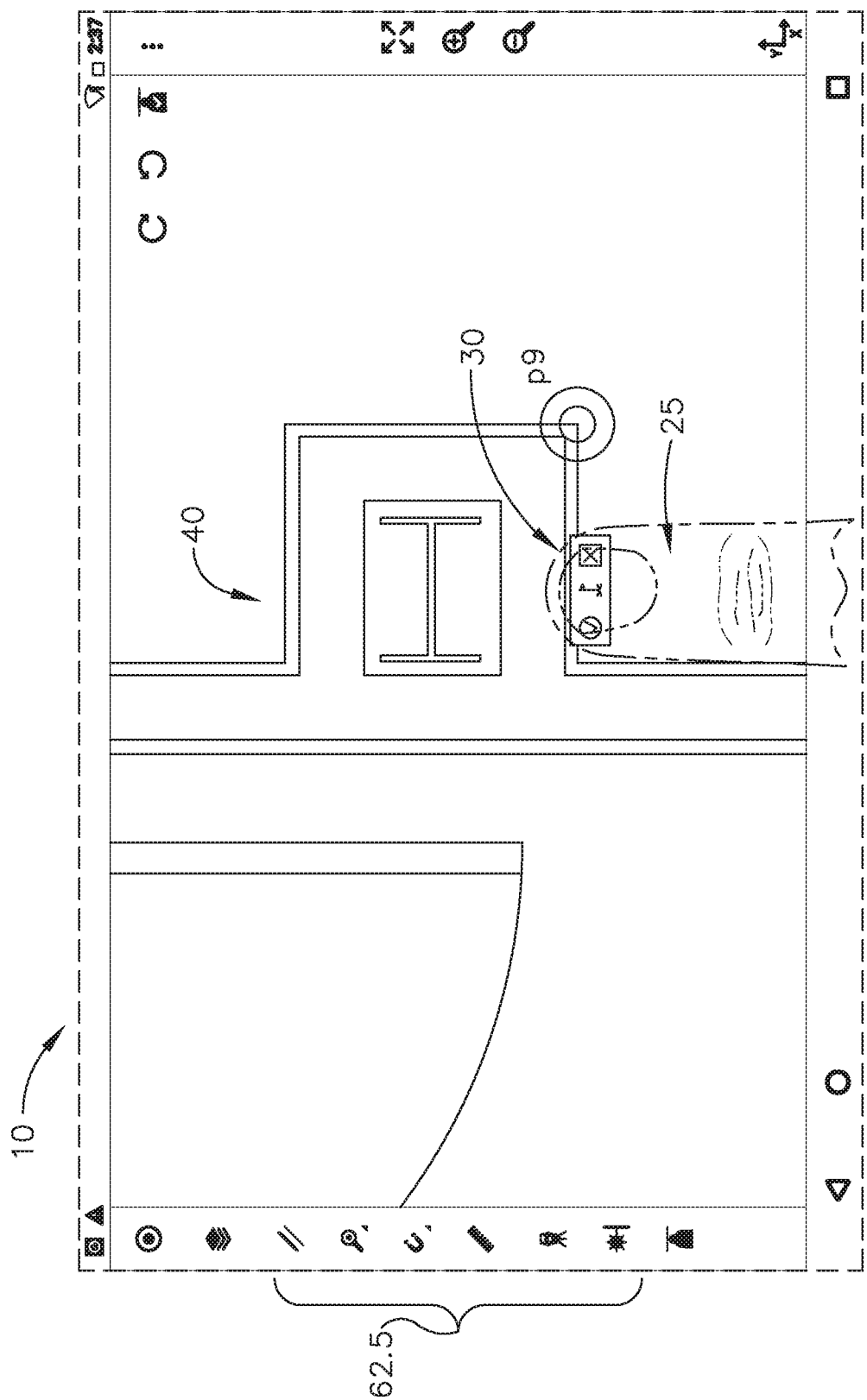
FIG. 26 is a diagrammatic view of a screen shot of the remote controller showing the user selecting the "CREATE & STAKE" icon for the second point of interest icon box of FIG. 25.
Figure 27:
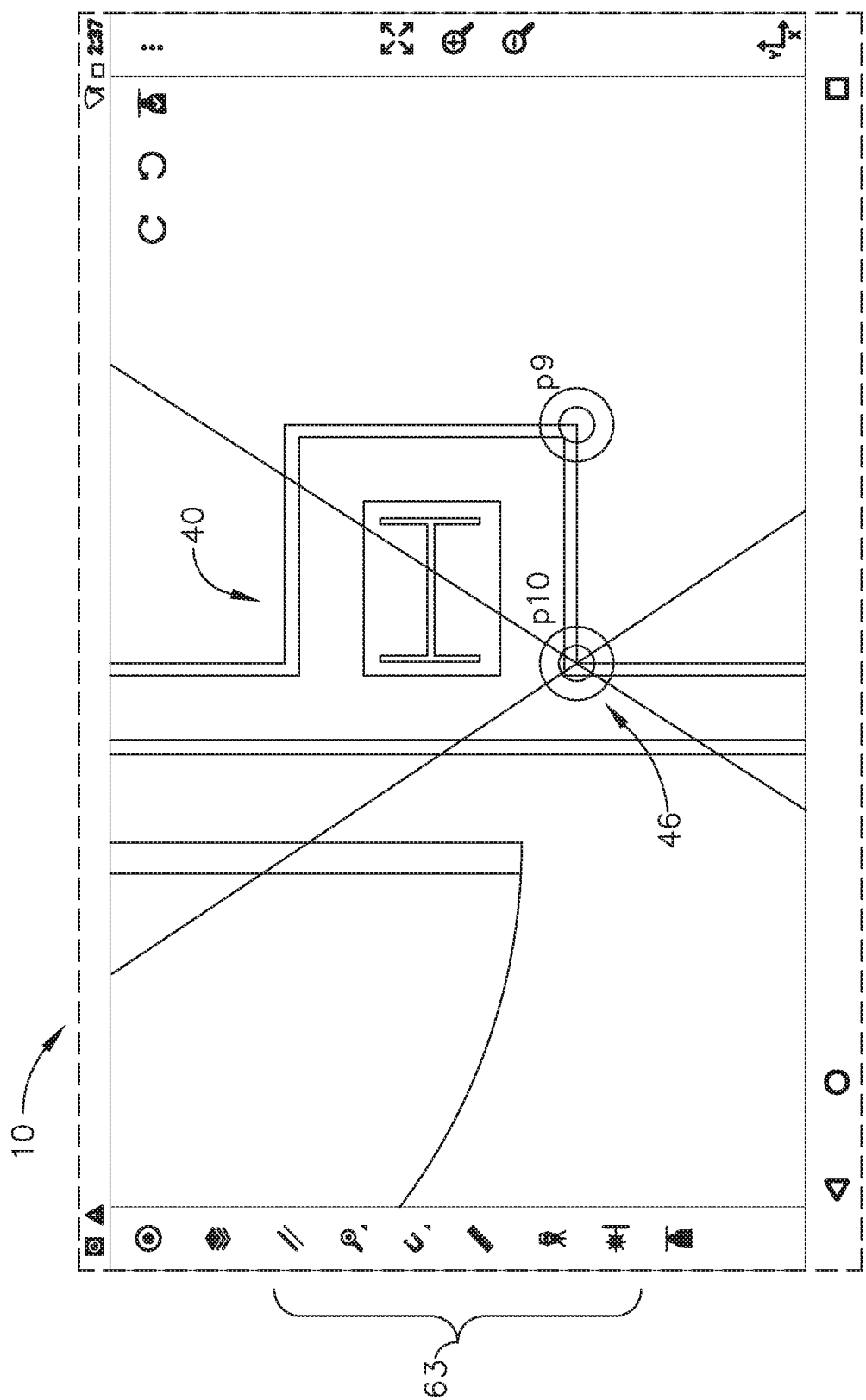
FIG. 27 is a diagrammatic view of a screen shot of the remote controller showing the result of selecting the "CREATE & STAKE" icon in FIG. 26, and now showing the new status of the second point of interest having been staked.

Moving on to FIG. 26, the user now taps the screen at the middle icon, which is the "CREATE & STAKE" icon, and this is the screen sequence designation #62.5. After tapping the center icon as shown in FIG. 26, the screenshot of FIG. 27 now appears and the next point of interest is designated as "p10" which is seen at the reference numeral 46 on FIG. 27. This is the screen sequence #63, which was also seen in FIG. 8. This screenshot of FIG. 27 shows that the two laser transmitters have now aimed their laser light lines so that they cross at the physical point of interest that corresponds to the point "p10" that is visible on the display screen of the remote controller tablet computer.

As can be seen from the above description, the operating software of the technology disclosed herein allows the user on the jobsite floor to create and stake one point of interest after another after another, without having to go back and perform separate "create" functions on a tablet or other computer that shows the virtual jobsite illustration on a CAD model. Not only is the user able to proceed from point to point, but the user can do so while zooming in on a particular small area of the jobsite floor without having to zoom in and zoom out to go from a create mode to a layout mode. This provides for a distinct increase in efficiency over the conventional technology that was described above in the BACKGROUND.

The operating software of the technology disclosed herein will be very popular with users who build interior walls, because such users like to specify and mark (stake) their points as a complete set. The present technology allows these users to view the CAD model on the remote controller and zoom in on the precise physical feature(s) that are to be laid out in a single work session. These users can not only select the exact points of interest for a particular physical feature (e.g., a stairwell), but they can also lay out and stake all of the associated points (i.e., as a complete set of points) at the same time that those points are being selected, without any back and forth to other operating modes of the software. Once certain points of the set are staked, the users can create chalk (snap) lines, and immediately build the walls from those snap lines.

The term "touchscreen display" is used throughout this written description. A touchscreen display actually combines two functions into a single overall hardware circuit: (1) there of course is a "display" or "screen", and (2) there is a user-controlled input circuit that acts as the "touch" sensing circuit for the overall touchscreen display.

Although most smart phones use touchscreen displays, not all portable (e.g., hand-held) computers use such touchscreen displays. As an alternative example of a "user-controlled input circuit," a portable computer could use a joystick with a thumb button to select a point on a standard (non-touchscreen) display. Other alternative examples of "user-controlled input circuits" (to act, for example, as user-controlled "pointing devices") include a touchpad, a mouse, a keypad, or a keyboard. Additionally, some computer display screens can provide a virtual keypad or virtual keyboard as an image on the display screen itself, rather than providing an actual "hardware" keypad or keyboard with that portable computer.

For purposes of definition, as used herein the term "touchscreen display" will include alternative devices including, but not limited to, a joystick, a touchpad, a mouse, a keypad, or a keyboard, and further could refer to a future type of user-controlled display with a "pointing" or "selecting" capability, including such display devices that have not yet been invented.

In the examples discussed above and illustrated in the drawings, the virtual jobsite illustrations (i.e., the virtual depiction of a jobsite on a computer display screen) all had the appearance of a two-dimensional ("2-D") CAD model. It will be understood that three-dimensional ("3-D") CAD model data files will also work well with the technology disclosed herein. The 2-D examples described above include situations where a user selects a point at an intersection of two lines. The same type of selection will be available using a 3-D CAD model. In addition, a 3-D CAD model will allow the user to rotate the virtual jobsite illustration on the display, so as to look at the points of interest from a different angle, if desired. Furthermore, a 3-D CAD model will also allow the user to "tilt" the virtual jobsite illustration—to see the third dimension—and then, for example, to search for points of interest that exist at intersections of three lines, i.e., at an intersection of lines in all three orthogonal dimensions, if desired. The same layout and staking functions of the executable software that runs on the remote controller will still be available when using a 3-D CAD model.

Two earlier patent documents are related to the technology disclosed herein, and are hereby incorporated by reference. These patent documents are: U.S. Pat. No. 8,087,176, titled "TWO DIMENSION LAYOUT AND POINT TRANSFER SYSTEM;" and U.S. Pat. No. 8,943,701, titled "AUTOMATED LAYOUT AND POINT TRANSFER SYSTEM." Both of these patent documents are assigned to Trimble Navigation Limited of Sunnyvale, Calif. (now known as Trimble, Inc.), and are incorporated herein by reference in their entirety. These patent documents disclose in detail the types of laser controllers and remote controllers that can be used to implement the technology disclosed herein, including a fan-beam laser controller for laser controllers 130 and 140 and a hand-held wireless tablet computer for the remote controller 600.

Other earlier patent documents disclose yet more advanced features that can be used with the technology disclosed herein, including patent application Ser. No. 15/351,170, filed on Nov. 14, 2016 (not yet published); and provisional patent application Ser. No. 62/447,078, filed on Jan. 17, 2017 (not yet published). These patent documents are assigned to Trimble Navigation Limited of Sunnyvale, Calif. (now known as Trimble, Inc.), and are incorporated herein by reference in their entirety.

Yet more patent documents disclose total stations and total tracking stations, including U.S. Pat. No. 5,313,409 and U.S. Pat. No. 6,175,328. These patent documents are owned by Trimble Navigation Limited of Sunnyvale, Calif. (now known as Trimble, Inc.), and are incorporated herein by reference in their entirety. (They are assigned to Spectra Precision AB or its predecessor company name, Geotronics. Spectra Precision AB is now owned by Trimble.)

Figure 28:
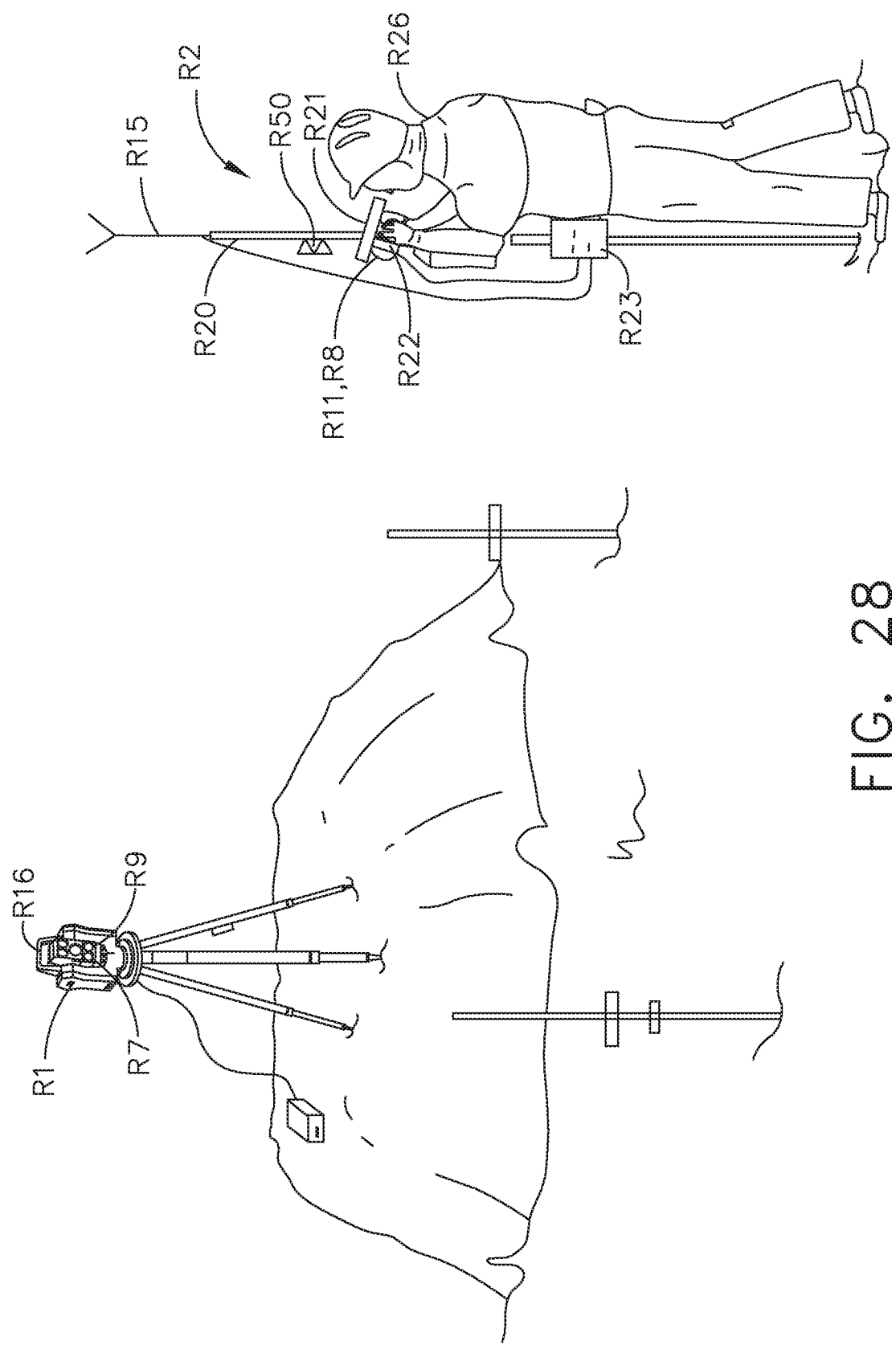
FIG. 28 illustrates a measuring arrangement at work in the open countryside, using a total station.

In the embodiment illustrated in FIG. 28, a target unit R2 (a "movable target") includes a staff R20 (a "prism pole"), provided with the antenna R15, and sighting means which includes a telescope R21 fitted with a vertical-angle indicator R22 of the kind which produces automatically an electrical signal indicative of the angular position of the telescope in relation to the vertical. A vertical-angle indicator of the pendulum type also has this facility. The vertical-angle indicator R22 is connected to a control box R23 which is mounted on the staff and which includes a control unit connected to a keyboard which can be manipulated by an operator R26 positioned by the side of the staff R20. The operator brings the telescope R21 into alignment with the measuring instrument on the measuring-instrument unit and depresses a key either on the sighting means R21, R22 or on the box R23, when he considers that alignment is correct.

Depression of the key causes the control unit to read-off the vertical-angle indicator and to produce a control signal. The digital angle-indicating signal is transmitted to the communication unit. This unit may comprise, for instance, a radio unit having circuits for modulating and transmitting angle information, e.g., on radio frequency, and synchronizing and control signals for transmission via the antenna R15. Other types of transmission systems are conceivable, for instance transmission via microwave links.

A communication unit for receiving and demodulating the signal arriving from the antenna R16 is connected to the control unit. This unit receives the angle information and calculates the vertical angle corresponding to the angular value obtained from the indicator R22 and to which the optical system of the instrument unit shall be aligned prior to receiving a signal from the light transmitter or the reflector R11. This angle will be $\pi$ rod (200 gons) minus the angular value obtained from the indicator R22. The control unit steers the servo motor to the calculated angle, via the drive unit, on the basis of the information obtained from the vertical angle indicator (with the digitally produced signal). This setting need only be effected with such accuracy as to ensure that the signal from the light transmitter R8 and the reflector R11 will fall within the aperture angle of the detector R7. The drive unit then causes the servo motor to rotate the instrument horizontally while, at the same time, reading-off a horizontal angle indicator with a digitally produced signal.

In FIG. 28, the light transmitter R8 of the target unit R2 is shown positioned on the sighting unit R21, R22, although said transmitter may equally well be placed directly on the staff R20. The light transmitter R8 may for instance be an IR-diode or a red light diode. The detector R7 in the measuring instrument unit R1 (a "total station") may, in one practical embodiment of the detector, have an optical field of view of one or more degrees. The light transmitter R8 may have a scattering angle of some tens of degrees. These values are only approximate and are fully contingent on the range desired of the system, i.e., on the practical applications for which the system is used.

In order to enable the instrument unit R1 to seek and find the target unit, the unit is thus directed vertically to the angle which corresponds to the angle indicated by the sighting means R21, R22, as described above. In this case, the instrument unit need only be rotated by the servo drive in a plane around its vertical axis, until the detector unit R7 observes the control signal from the light transmitting unit R8 and the reflected signal from the unit R11, whereupon the servo drive in the horizontal direction is stopped. If this rotation is rapid, the instrument unit will pass the target, although the position of the target can be registered by the control unit, which first stops and then rotates the instrument unit R1 back onto the target. The control unit then passes to its target tracking mode and controls the servo motors and of the instrument unit R1 in a manner described in more detail hereinbelow, so as to track the target.

Both the signal from the light transmitting unit R8 and the reflected signal from the unit R11 must be detected by the detector R7 during the target seeking sequence in order to discriminate the instrument unit from locking to false targets, as will be discussed in more detail hereinbelow. During the target tracking sequence, when the target is moved in relation to the instrument, and the target tracking normally is based on the signal from the light transmitting unit R8, because the target unit is rather close to the instrument unit, it is essential also to have the reflected signal from the prism R11 detected by the control and computing unit, even though it is not used for the actual tracking, because in this case the tracking could instantly be switched over to tracking based on the reflected beam from the prism R11, if the signal from the unit R8 should be lost. The target unit staff could sway when moved. Then, there is a risk that the light transmitting unit could be turned such that its light lobe is moved out of contact with the detector R7. The direction of the reflected light beam from the prism will be kept essentially antiparallel to the light beam from the light transmitter R9 even for rather extensive turning of the staff, at least compared to what can be permitted for the unit R8. However, when actual measurements of measuring points are to be made, i.e. not only measurements made during movement in order to up-date positional values for the control and computing unit, the direction of the instrument should preferably be based on the signal from the light transmitting unit R8 onto the detector R7, i.e., if this is available to a sufficient extent.

A conventional EDM-device (distance meter) is also directed onto the cube corner prism R11. Therefore, a parallax error regarding the instrument direction is introduced in the system when the target and hence the prism R11 comes too close to the measuring-instrument unit R1. It is, however, possible to provide two different sets of prisms, one (R11) for the target seeking and tracking beam and another (R50) (see FIG. 28) for the EDM-device, if the target seeking and tracking beam and the EDM-device beam have different wave-lengths and the prisms are provided with wave-length filters adapted to the wave-length of the very light beam they are intended to reflect. However, it is rather expensive to have two such reflection systems on the target unit and the filters will also introduce an attenuation of the reflected light beam. Thus, it is preferred not to have a separate prism arrangement R50 for the EDM-device, but rather to use one and the same prism R11 for both the instrument and the target seeking and tracking device.

It will be understood that the logical operations described in relation to the flow charts of FIGS. 18-19 can be implemented using sequential logic (such as by using microprocessor technology), or using a logic state machine, or perhaps by discrete logic; it even could be implemented using parallel processors. One preferred embodiment may use a microprocessor or microcontroller (e.g., microprocessors 410 or 610) to execute software instructions that are stored in memory cells within an ASIC. In fact, the entire microprocessor 410 or 610, along with RAM and executable ROM, may be contained within a single ASIC, in one mode of the technology disclosed herein. Of course, other types of circuitry could be used to implement these logical operations depicted in the drawings without departing from the principles of the technology disclosed herein. In any event, some type of processing circuit will be provided, whether it is based on a microprocessor, a microcomputer, a microcontroller, a logic state machine, by using discrete logic elements to accomplish these tasks, or perhaps by a type of computation device not yet invented; moreover, some type of memory circuit will be provided, whether it is based on typical RAM chips, EEROM chips (including Flash memory), by using discrete logic elements to store data and other operating information, or perhaps by a type of memory device not yet invented.

It will also be understood that the precise logical operations depicted in the flow charts of FIGS. 18-19, and discussed above, could be somewhat modified to perform similar, although perhaps not exact, functions without departing from the principles of the technology disclosed herein. The exact nature of some of the decision steps and other commands in these flow charts are directed toward specific future models of sensing and control system devices used with earthmoving equipment (those involving laser receivers sold by Trimble, Inc., for example) and certainly similar, but somewhat different, steps would be taken for use with other models or brands of sensing or control systems in many instances, with the overall inventive results being the same.

It will be further understood that any type of product described herein that has moving parts, or that performs functions (such as computers with processing circuits and memory circuits), should be considered a "machine," and not merely as some inanimate apparatus. Such "machine" devices should automatically include power tools, printers, electronic locks, and the like, as those example devices each have certain moving parts. Moreover, a computerized device that performs useful functions should also be considered a machine, and such terminology is often used to describe many such devices; for example, a solid-state telephone answering machine may have no moving parts, yet it is commonly called a "machine" because it performs well-known useful functions.

It will be understood that the various components that are described and/or illustrated herein can be fabricated in various ways, including in multiple parts or as a unitary part for each of these components, without departing from the principles of the technology disclosed herein. For example, a component that is included as a recited element of a claim hereinbelow may be fabricated as a unitary part; or that component may be fabricated as a combined structure of several individual parts that are assembled together. But that "multi-part component" will still fall within the scope of the claimed, recited element for infringement purposes of claim interpretation, even if it appears that the claimed, recited element is described and illustrated herein only as a unitary structure.

All documents cited in the Background and in the Detailed Description are, in relevant part, incorporated herein by reference; the citation of any document is not to be construed as an admission that it is prior art with respect to the technology disclosed herein.

The foregoing description of a preferred embodiment has been presented for purposes of illustration and description. It is not intended to be exhaustive or to limit the technology disclosed herein to the precise form disclosed, and the technology disclosed herein may be further modified within the spirit and scope of this disclosure. Any examples described or illustrated herein are intended as non-limiting examples, and many modifications or variations of the examples, or of the preferred embodiment(s), are possible in light of the above teachings, without departing from the spirit and scope of the technology disclosed herein. The embodiment(s) was chosen and described in order to illustrate the principles of the technology disclosed herein and its practical application to thereby enable one of ordinary skill in the art to utilize the technology disclosed herein in various embodiments and with various modifications as are suited to particular uses contemplated. This application is therefore intended to cover any variations, uses, or adaptations of the technology disclosed herein using its general principles. Further, this application is intended to cover such departures from the present disclosure as come within known or customary practice in the art to which this technology disclosed herein pertains and which fall within the limits of the appended claims.

What is claimed is:

1. A method for using a layout and point transfer system, said method comprising:
   (a) providing at least one laser controller, said at least one laser controller including: (i) a laser light transmitter that emits visible laser light, said laser light transmitter being rotatable about a substantially vertical axis; (ii) an electronic angle measuring instrument; and (iii) a first processing circuit, a first memory circuit, a first wireless communications circuit, and a first input/output interface circuit;
   (b) providing a remote controller, which includes: a second processing circuit, a second memory circuit, a second wireless communications circuit, a display, a user-controlled input circuit, and a second input/output interface circuit, wherein said at least one laser controller and said remote controller communicate with one another by use of said first and second wireless communications circuits;
   (c) placing said at least one laser controller on a jobsite surface in a work area, and setting up said at least one laser controller so that, in terms of jobsite coordinates, a position of said at least one laser controller on said jobsite surface is determined;
   (d) executing a computer program using said remote controller, which displays a virtual jobsite illustration on said display;
   (e) selecting, using said display and said user-controlled input circuit, a specific point of interest on said virtual jobsite illustration, and, without changing operating modes, virtually staking said specific point of interest on said virtual jobsite illustration; and
   (f) automatically indicating, on said jobsite surface, said specific point of interest to be staked, by aiming the laser light transmitter of said at least one laser controller directly at an azimuth angle of said specific point of interest on the jobsite surface.

2. The method of claim 1, wherein said selecting step comprises:
   (a) a human user first selects said specific point of interest, using said display and said user-controlled input circuit;
   (b) said computer program causes said display to show a point symbol to confirm said selected specific point of interest to the user;
   (c) said computer program causes said display to show a menu box having a CREATE & STAKE symbol; and
   (d) the user selects said CREATE & STAKE symbol, and the software automatically displays a new point designator symbol representing said selected specific point of interest on the display.

3. The method of claim 1, further comprising the steps of:
   (a) physically staking said specific point of interest on the jobsite surface;
   (b) without referring to a separate point list file, selecting, using said display and said user-controlled input circuit, a second specific point of interest on said virtual jobsite illustration, and virtually staking said second specific point of interest on said virtual jobsite illustration;
   (c) automatically indicating, on said jobsite surface, said second specific point of interest to be physically staked, by aiming the laser light transmitter of said at least one laser controller directly at an azimuth angle of said second specific point of interest on the jobsite surface; and
   (d) physically staking said second specific point of interest on the jobsite surface.

4. The method of claim 3, further comprising the step of: after a new point designation is displayed, showing on said display at least one virtual laser transmitter light line that becomes aimed at the new point designator symbol representing the selected specific point of interest.

5. The method of claim 1, wherein: said at least one laser controller comprises a total station, and said laser light transmitter comprises a visible pointing laser beam that aims directly at said specific point of interest on the jobsite surface, to provide a visible indication on said jobsite surface as to where said specific point of interest should be physically staked.

6. The method of claim 1, wherein:
   (a) said at least one laser controller comprises two laser transmitters that are positioned at separate positions on said jobsite surface, each of said two laser transmitters emitting a visible, vertical laser plane that rotates about a vertical axis; and
   (b) the step of aiming the laser light transmitter of said at least one laser controller directly at an azimuth angle of said specific point of interest on the jobsite surface comprises:
      (i) aiming said vertical laser plane of a first of said two laser transmitters directly at said specific point of interest on the jobsite surface, so that a first visible laser light line is produced upon said jobsite surface and directly crosses said specific point of interest;
      (ii) aiming said vertical laser plane of a second of said two laser transmitters directly at said specific point of interest on the jobsite surface, so that a second visible laser light line is produced upon said jobsite surface and directly crosses said specific point of interest; and
      (iii) an intersection of said first visible laser light line and said second visible laser light line provides a visible indication on said jobsite surface as to where said specific point of interest should be physically staked.

7. The method of claim 1, wherein said user-controlled input circuit comprises at least one of:
   (a) a touch-sensing circuit that communicates with said display, to create a touchscreen display;
   (b) a joystick;
   (c) a touchpad;
   (d) a mouse;
   (e) a keypad; and
   (f) a keyboard.

8. A method for using a layout and point transfer system, said method comprising:
   (a) providing a laser controller, said laser controller including: (i) an electronic distance measuring instrument; (ii) an electronic angle measuring instrument; and (iii) a first processing circuit, a first memory circuit, a first wireless communications circuit, and a first input/output interface circuit;

(b) providing a remote controller, which includes: a second processing circuit, a second memory circuit, a second wireless communications circuit, a display, a user-controlled input circuit, and a second input/output interface circuit, wherein said laser controller and said remote controller communicate with one another by use of said first and second wireless communications circuits;

(c) providing a movable target that is controlled by a human user;

(d) placing said laser controller on a jobsite surface in a work area, and setting up said laser controller so that, in terms of jobsite coordinates, a position of said laser controller on said jobsite surface is determined;

(e) executing a computer program using said remote controller, which displays a virtual jobsite illustration on said display;

(f) selecting, using said display and said user-controlled input circuit, a specific point of interest on said virtual jobsite illustration, and, without changing operating modes, virtually staking said specific point of interest on said virtual jobsite illustration; and (g) automatically indicating said specific physical point of interest to be staked:
  (i) by aiming the electronic distance measuring instrument of said laser controller directly at said movable target as the human user moves the movable target;
  (ii) by providing directions to said user to guide movements of the movable target toward said specific point of interest on the jobsite surface; and
  (iii) by providing an indication to said user that the movable target is now placed at said specific point of interest on the jobsite surface.

9. The method of claim 8, wherein said selecting step comprises:
  (a) a human user first selects said specific point of interest on said display;
  (b) said computer program causes said display to show a point symbol to confirm said selected specific point of interest to the user;
  (c) said computer program causes said display to show a menu box having a CREATE & STAKE symbol; and
  (d) the user selects said CREATE & STAKE symbol, and the software automatically displays a new point designator symbol representing said selected specific point of interest on the display.

10. The method of claim 8, further comprising the steps of:
  (a) physically staking said specific point of interest on the jobsite surface;
  (b) without referring to a separate point list file, selecting, using said display and said user-controlled input circuit, a second specific point of interest on said virtual jobsite illustration, and virtually staking said second specific point of interest on said virtual jobsite illustration;
  (c) automatically indicating, on said jobsite surface, said second specific point of interest to be physically staked, by aiming the electronic distance measuring instrument of said laser controller directly at an azimuth angle of said second specific point of interest on the jobsite surface; and
  (d) physically staking said second specific point of interest on the jobsite surface.

11. The method of claim 8, wherein said the movable target comprises at least one of: (a) a prism pole; or (b) a substantially vertical surface.

12. The method of claim 8, wherein said laser controller comprises a total station that aims its laser distance measuring instrument at a prism on a prism pole, and determines the position of said prism pole to guide the user until the prism pole is placed at the correct azimuth angle and at the correct distance from the laser controller, to indicate where said specific point of interest should be physically staked.

13. The method of claim 8, wherein the step of automatically indicating said specific physical point of interest comprises one of:
  (a) visually displaying a position of the movable target on said display of said remote controller;
  (b) announcing a position of the movable target using an audible output located on said remote controller;
  (c) announcing a position of the movable target using an audible output located on said laser controller;
  (d) announcing a position of the movable target using a light source located on said remote controller; and
  (e) announcing a position of the movable target using a light source located on said laser controller.

14. The method of claim 8, wherein said user-controlled input circuit comprises at least one of:
  (a) a touch-sensing circuit that communicates with said display, to create a touchscreen display;
  (b) a joystick;
  (c) a touchpad;
  (d) a mouse;
  (e) a keypad; and
  (f) a keyboard.

15. A method for using a layout and point transfer system, said method comprising:
  (a) providing a laser controller, said laser controller including: (i) an electronic distance measuring instrument; (ii) an electronic angle measuring instrument; (iii) a laser light transmitter that emits visible laser light, said laser light transmitter being rotatable about a substantially vertical axis; and (iv) a first processing circuit, a first memory circuit, a first wireless communications circuit, and a first input/output interface circuit;
  (b) providing a remote controller, which includes: a second processing circuit, a second memory circuit, a second wireless communications circuit, a display, a user-controlled input circuit, and a second input/output interface circuit, wherein said laser controller and said remote controller communicate with one another by use of said first and second wireless communications circuits;
  (c) providing a movable target that is controlled by a human user;
  (d) placing said laser controller on a jobsite surface in a work area, and setting up said laser controller so that, in terms of jobsite coordinates, a position of said laser controller on said jobsite surface is determined;
  (e) executing a computer program using said remote controller, which displays a virtual jobsite illustration on said display;
  (f) selecting, using said display and said user-controlled input circuit, a specific point of interest on said virtual jobsite illustration, and, without changing operating modes, virtually staking said specific point of interest on said virtual jobsite illustration; and
  (g) automatically indicating said specific physical point of interest to be staked:

(i) by aiming the electronic distance measuring instrument of said laser controller directly at an azimuth angle of said specific point of interest on the jobsite surface;

(ii) by aiming the laser light transmitter along the same azimuth angle as said electronic distance measuring instrument, thereby emitting a visible laser light line upon said jobsite surface that directly crosses said specific point of interest; and (iii) by the human user moving the movable target along said visible laser light line until the movable target is placed at said specific physical point of interest on the jobsite surface, as indicated by said electronic distance measuring instrument.

16. The method of claim 15, wherein said selecting step comprises:

(a) a human user first selects said specific point of interest, using said display and said user-controlled input circuit;

(b) said computer program causes said display to show a point symbol to confirm said selected specific point of interest to the user;

(c) said computer program causes said display to show a menu box having a CREATE & STAKE symbol; and (d) the user selects said CREATE & STAKE symbol, and the software automatically displays a new point designator symbol representing said selected specific point of interest on the display.

17. The method of claim 15, further comprising the steps of:

(a) physically staking said specific point of interest on the jobsite surface;

(b) without referring to a separate point list file, selecting, using said display and said user-controlled input circuit, a second specific point of interest on said virtual jobsite illustration, and virtually staking said second specific point of interest on said virtual jobsite illustration;

(c) automatically indicating, on said jobsite surface, said second specific point of interest to be physically staked, by aiming the electronic distance measuring instrument of said laser controller directly at an azimuth angle of said second specific point of interest on the jobsite surface; and (d) physically staking said second specific point of interest on the jobsite surface.

18. The method of claim 15, wherein said the movable target comprises a substantially vertical surface.

19. The method of claim 15, wherein the step of automatically indicating said specific physical point of interest comprises one of:

(a) visually displaying a position of the movable target on said display of said remote controller;

(b) announcing a position of the movable target using an audible output located on said remote controller;

(c) announcing a position of the movable target using an audible output located on said laser controller;

(d) announcing a position of the movable target using a light source located on said remote controller; and (e) announcing a position of the movable target using a light source located on said laser controller.

20. The method of claim 15, wherein said laser light transmitter emits a visible laser plane that is vertical and rotatable, which produces a visible laser light line on the jobsite surface.

21. The method of claim 15, wherein said user-controlled input circuit comprises at least one of:

(a) a touch-sensing circuit that communicates with said display, to create a touchscreen display;

(b) a joystick;

(c) a touchpad;

(d) a mouse;

(e) a keypad; and (f) a keyboard.

22. A layout and point transfer system, said system comprising:

(a) at least one laser controller, said at least one laser controller including: (i) a laser light transmitter that emits visible laser light, said laser light transmitter being rotatable about a substantially vertical axis; (ii) an electronic angle measuring instrument; and (iii) a first processing circuit, a first memory circuit, a first wireless communications circuit, and a first input/output interface circuit; and (b) a remote controller, which includes: a second processing circuit, a second memory circuit, a second wireless communications circuit, a display, a user-controlled input circuit, and a second input/output interface circuit, wherein said at least one laser controller and said remote controller communicate with one another by use of said first and second wireless communications circuits;

wherein:

(c) after said at least one laser controller is placed on a physical jobsite surface in a work area, said system is configured:

(i) to set up said at least one laser controller so that, in terms of jobsite coordinates, a position of said at least one laser controller on said jobsite surface is determined;

(ii) to execute a computer program using said remote controller, which displays a virtual jobsite illustration on said display;

(iii) to select, using said display and said user-controlled input circuit, a specific point of interest on said virtual jobsite illustration;

(iv) without changing operating modes, to virtually stake said specific point of interest on said virtual jobsite illustration; and (v) to automatically indicate, on said jobsite surface, said specific point of interest to be staked, by aiming the laser light transmitter of said at least one laser controller directly at an azimuth angle of said specific point of interest on the jobsite surface.

23. The system of claim 22, wherein said system is further configured:

(a) without referring to a separate point list file, to select, using said display and said user-controlled input circuit, a second specific point of interest on said virtual jobsite illustration;

(b) to virtually stake said second specific point of interest on said virtual jobsite illustration; and (c) to automatically indicate, on said jobsite surface, said second specific point of interest to be physically staked, by aiming the laser light transmitter of said at least one laser controller directly at an azimuth angle of said second specific point of interest on the jobsite surface.

24. The system of claim 22, wherein said user-controlled input circuit comprises at least one of:

(a) a touch-sensing circuit that communicates with said display, to create a touchscreen display;

(b) a joystick;

(c) a touchpad;

(d) a mouse;

(e) a keypad; and
(f) a keyboard.

\* \* \* \* \*